United States Patent
Stanke et al.

(10) Patent No.: US 7,924,422 B2
(45) Date of Patent: Apr. 12, 2011

(54) CALIBRATION METHOD FOR OPTICAL METROLOGY

(75) Inventors: Fred Stanke, San Jose, CA (US); Adam Norton, Palo Ato, CA (US); Holger Tuitje, Fremont, CA (US)

(73) Assignee: Tokyo Electron Limited (JP)

( * ) Notice: Subject to any disclaimer, the term of this patent is extended or adjusted under 35 U.S.C. 154(b) by 323 days.

(21) Appl. No.: 12/369,947

(22) Filed: Feb. 12, 2009

(65) Prior Publication Data
US 2010/0201981 A1    Aug. 12, 2010

(51) Int. Cl.
*G01J 3/28* (2006.01)
(52) U.S. Cl. .......................................... 356/326
(58) Field of Classification Search ........... 356/326–328
See application file for complete search history.

(56) References Cited

U.S. PATENT DOCUMENTS

| | | | |
|---|---|---|---|
| 4,997,281 A | | 3/1991 | Stark |
| 5,014,216 A | * | 5/1991 | Stafford et al. ............... 356/328 |
| 5,139,335 A | | 8/1992 | Lundeen et al. |
| 5,420,681 A | | 5/1995 | Woodruff |
| 5,568,400 A | * | 10/1996 | Stark et al. ...................... 702/85 |
| 6,122,052 A | | 9/2000 | Barnes et al. |
| 6,891,626 B2 | | 5/2005 | Niu et al. |
| 6,943,900 B2 | | 9/2005 | Niu et al. |
| 2004/0257563 A1 | | 12/2004 | Miller et al. |
| 2004/0267397 A1 | | 12/2004 | Doddi et al. |
| 2006/0176480 A1 | * | 8/2006 | Toth et al. ....................... 356/328 |
| 2009/0103088 A1 | * | 4/2009 | Delmas et al. ................ 356/328 |

OTHER PUBLICATIONS

Heaney et al., "Order-sorting filter transmittance measured with an array detector", Aug. 1993, Optical Engineering, vol. 32, No. 8, pp. 1827-1834.*
U.S Appl. No. 12/057,346, filed Mar. 27, 2008, for Tian et al.
U.S Appl. No. 12/057,332, filed Mar. 27, 2008, for Tian et al.

* cited by examiner

*Primary Examiner* — Kara E Geisel

(57) ABSTRACT

A zoned order sorting filter for a spectrometer in a semiconductor metrology system is disclosed with reduced light dispersion at the zone joints. The order sorting filter comprises optically-transparent layers deposited underneath, or on top of thin-film filter stacks of the order sorting filter zones, wherein the thicknesses of the optically-transparent layers are adjusted such that the total optical lengths traversed by light at a zone joint are substantially equal in zones adjacent the zone joint. A method for wavelength to detector array pixel location calibration of spectrometers is also disclosed, capable of accurately representing the highly localized nonlinearities of the calibration curve in the vicinity of zone joints of an order sorting filter.

16 Claims, 8 Drawing Sheets

CALIBRATION METHOD FOR OPTICAL METROLOGY

CROSS-REFERENCE TO RELATED APPLICATIONS

This application is related to co-pending U.S. patent application Ser. No. 12/369,905 entitled "DIFFRACTION ORDER SORTING FILTER FOR OPTICAL METROLOGY" (Ref. No. TTI-214), filed on even date herewith, the entire contents of which are herein incorporated by reference in their entirety.

BACKGROUND OF THE INVENTION

1. Field of the Invention

This invention relates to optical metrology used in the manufacturing of semiconductor devices, and more particularly to a zoned diffraction order sorting filter for spectrometers used in semiconductor optical metrology systems, and to a method for wavelength calibration of spectrometers with zoned order sorting filters.

2. Description of Related Art

One type of optical metrology involves directing an incident beam at a structure on a workpiece, measuring the resulting diffraction signal, and analyzing the measured diffraction signal to determine various characteristics of the structure. The workpiece can be a semiconductor wafer or substrate, a photomask, or a magnetic medium. In manufacturing of workpieces, periodic gratings are typically used for quality assurance. For example, one typical use involves fabricating a periodic grating in proximity to the operating structure of a semiconductor chip. The periodic grating is then illuminated with electromagnetic radiation, and the electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional system, the diffraction signal collected from illuminating the periodic grating (i.e. the measured diffraction signal) is compared to a library of simulated diffraction signals. Each simulated diffraction signal in the library is associated with a hypothetical profile, i.e. cross-section, of the periodic grating. When a match is made between the measured diffraction signal and one of the simulated diffraction signals in the library, the hypothetical profile associated with the simulated diffraction signal is presumed to represent the actual profile of the periodic grating. The hypothetical profiles, which are used to generate the simulated diffraction signals, are generated based on a profile model that characterizes the structure to be examined. Thus, in order to accurately determine the profile of the structure using optical metrology, a profile model that accurately characterizes the structure should be used.

With increased requirements for throughput, decreasing size of the test structures, smaller illuminated spot sizes, and lower cost of ownership, there is greater need to optimize designs of optical metrology systems to meet these design goals. Characteristics of the optical metrology system including sampling time, range of measurement capabilities, accuracy and repeatability of diffraction signal measurements are essential to meeting these ever-increasing requirements.

Spectrometers are used to measure diffraction signals over a wide range of wavelengths, from the near-infrared (NIR), over visible light (VIS), and ultraviolet (UV), to the deep ultraviolet (DUV) parts of the electromagnetic spectrum. A spectrometer typically employs a blazed diffraction grating to disperse an optical signal onto an array detector capable of measuring the intensity of different wavelengths present in the optical signal, i.e. the diffraction signal. A diffraction grating disperses the optical signal into a multitude of diffraction orders, of which typically only the first order is used to perform the actual diffraction signal measurement and matching against a diffraction signal library. However, when the wavelength range of the diffraction signal exceeds one octave, as is typically the case in semiconductor optical metrology systems, the diffraction orders generated by the grating start to overlap each other. Due to diffraction order overlap, in addition to measuring the intensity of the first diffraction order at a calibrated wavelength $\lambda$, the same array detector location, i.e. pixel, would also see and detect the second diffraction order intensity of wavelength $\lambda/2$. In the case of very large wavelength ranges, it may also see and detect the third diffraction order intensity of wavelength $\lambda/3$, etc. To prevent the detection of unwanted higher diffraction orders at any array detector pixel, an order sorting filter (OSF) may be employed. In the simplest embodiment, an OSF is a suitable optical long-pass or band-pass filter installed in front of the array detector, which prevents shorter wavelengths of the higher diffraction orders from reaching the detector. The OSF may comprise multiple zones spanning the length of the array detector, where each zone has different passband characteristics, or it may have continuously-changing passband characteristics. A zoned OSF is simpler and relatively inexpensive compared to the continuously-variable type, and is typically used for compact and fast spectrometers.

One of the drawbacks of a zoned OSF is the appearance of anomalies in measured diffraction signals at wavelengths in the vicinity of joints between OSF zones. In a zoned OSF filter, each zone is typically implemented as a thin-film stack filter on a common optically-transparent substrate. The inventors have realized that due to varying passband characteristics of the zones, the optical length traversed by the light beam through the thin-film stack filter of each zone also, in general, varies. The sharp change of traversed optical length at the zone joint may cause unwanted dispersion of light, such that light incident at the zone joint is spread sideways onto multiple pixels of the array detector. In addition to spreading onto multiple adjacent pixels, this dispersion may cause a sideways shift of the centroid of the image projected upon the detector. The inventors believe this image spreading and shifting to be the main cause of unwanted localized anomalies in the measured diffraction signals at the zone joints. Thus, to improve accuracy of measured diffraction signals, there exists a need to minimize unwanted dispersion at zone joints in an OSF, or otherwise correct measured diffraction signals affected by dispersion at OSF zone joints.

SUMMARY OF THE INVENTION

According to an embodiment of the invention, an order sorting filter (OSF) is provided where underlayers are deposited underneath the thin-film stack filters of all OSF zones, where the thicknesses of the underlayers of each pair of adjacent zones are adjusted such that the total optical lengths traversed by light of the wavelength falling at each zone joint are substantially equal in the two zones adjacent the joint, or alternatively, that the beams of the wavelength falling at each zone joint emerge in phase from the two zones adjacent the zone joint. To minimize internal reflections inside the filter, the index of refraction of the underlayer material must be chosen to substantially match that of the common optically-transparent OSF substrate.

In an alternative embodiment, to maximize, for example, transmission of the OSF in the UV and DUV parts of the spectrum, the underlayer is omitted from a zone corresponding to those parts of the spectrum, and the underlayer thickness in the adjacent zone is adjusted such that the total optical lengths traversed by light of the wavelength falling at the zone joint are substantially equal in the two zones adjacent the joint, or alternatively, that the beams of the wavelength falling at the zone joint emerge in phase from the two zones adjacent the zone joint.

In yet another alternative embodiment, to maximize, for example, transmission of the OSF in the UV and DUV parts of the spectrum, the thin-film stack filter is omitted from a zone corresponding to those parts of the spectrum, but an underlayer is deposited in this zone, the thickness of which is adjusted such that the total optical lengths traversed by light falling at a zone joint are substantially equal in the two zones adjacent the joint, or alternatively, that the beams of the wavelength falling at the zone joint emerge in phase from the two zones adjacent the zone joint.

In accordance with another embodiment of the invention, OSF zone thin-film stack filters themselves are designed and/or modified such that the total optical lengths traversed by light of the wavelength falling at each zone joint are substantially equal in the two zones adjacent the joint, or alternatively, that the beams of the wavelength falling at each zone joint emerge in phase from the two zones adjacent the zone joint, both in addition to having the required passband characteristics to suppress higher diffraction orders from reaching the array detector. The design modification can be achieved by addition of layers, or modifying properties, i.e. thicknesses and optical constants, of existing thin-film stack filter layers.

According to a further embodiment of the invention, a method is provided for wavelength vs. array detector pixel location calibration which can accommodate and correct for dispersion at zone joints in an OSF filter, by utilizing separate calibration curves in the vicinity of zone joints, to accommodate for the highly nonlinear nature of the wavelength to pixel location calibration curve at and/or in the vicinity of zone joints.

BRIEF DESCRIPTION OF THE DRAWINGS

A more complete appreciation of the invention and many of the attendant advantages thereof will become readily apparent with reference to the following detailed description, particularly when considered in conjunction with the accompanying drawings, in which.

DETAILED DESCRIPTION OF EXEMPLARY EMBODIMENTS

In the following description, in order to facilitate a thorough understanding of the invention and for purposes of explanation and not limitation, specific details are set forth, such as a particular geometry of the metrology system and descriptions of various components and processes. However, it should be understood that the invention may be practiced in other embodiments that depart from these specific details.

Figure 1:
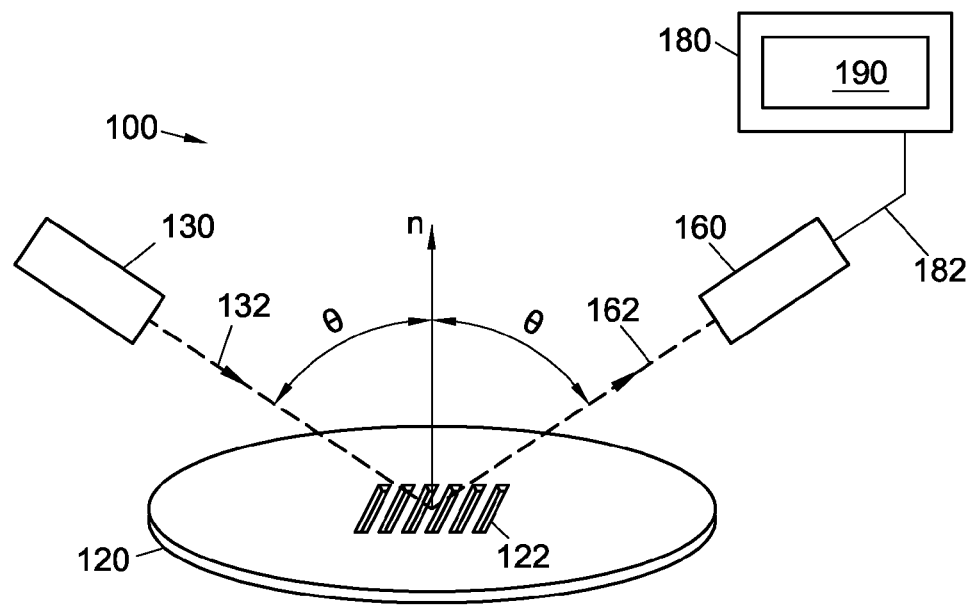
FIG. 1 is a basic schematic representation of an optical metrology system utilized to determine profiles of structures formed on a workpiece, such as a semiconductor wafer or substrate.

FIG. 1 is a basic schematic representation of an embodiment of an optical metrology system that can be utilized to determine profiles of structures on a substrate. Optical metrology system 100 comprises a metrology beam source 130 which projects an illumination beam 132 towards metrology target structure 122 formed on semiconductor substrate 120. The illumination beam 132 illuminates the metrology target structure 122 at an incidence angle θ measured from the vertical, i.e. normal direction to the surface of semiconductor substrate 120. Incidence angle θ can vary from 0°, i.e. normal incidence, to about 80°, depending on the type of profile measurements being made, capabilities of the available metrology system hardware, etc. Light reflected and diffracted by the metrology target structure 122 forms the detection beam 162 that is collected and measured by a metrology beam receiver 160, which generates a measured diffraction signal 182. Optical metrology system 100 can be configured as a reflectometer, an ellipsometer, a scatterometer, or any other optical device capable of measuring the diffraction signal 182. Measured diffraction signal 182 is transmitted to a processor 180. Processor 180 compares the measured diffraction signal 182 against simulated diffraction signals and their associated hypothetical profiles representing various combinations of profile dimensions of metrology target structure 122, all generated by a simulator 190. Simulator 190 can be a library comprising a database of simulated diffraction signals, or a machine-learning system capable of generating simulated diffraction signals, or alternatively an on-demand (i.e. real time, regression) solver capable of generating simulated diffraction signals. Once a simulated diffraction signal is identified that best matches the measured diffraction signal 182, it is assumed that the actual profile dimensions of metrology target structure 122 correspond to those associated with the best-matching simulated diffraction signal. An optical metrology system 100 and the process of library generation is described in more detail in U.S. Pat. No. 6,943,900, entitled "Generation of a library of periodic grating diffraction signals", issued on Sep. 13, 2005, which is incorporated herein by reference in its entirety.

In one embodiment, simulated diffraction signals can be generated by applying Maxwell's equations and using numerical analysis techniques to solve Maxwell's equations. It should be noted that various numerical analysis techniques, including variations of RCWA, can be used. A more detailed description of RCWA can be found in U.S. Pat. No. 6,891,626, entitled "Caching of intra-layer calculations for rapid rigorous coupled-wave analyses", issued on May 10, 2005, which is incorporated herein by reference in its entirety.

In another embodiment, simulated diffraction signals can be generated using a machine-learning system (MLS). Prior to generating simulated diffraction signals, the MLS is trained using known input data comprising profiles of structures of known dimensions, and output data comprising diffraction signals corresponding to those known profiles. Simulated diffraction signals can be generated using an MLS employing machine-learning algorithms, such as back-propagation, radial basis function, support vector, kernel regression, and the like. For a more detailed description of machine learning systems and algorithms, see U.S. patent application Ser. No. 10/608,300, entitled "Optical metrology of structures formed on semiconductor wafers using machine learning systems", filed on Jun. 27, 2003, which is incorporated herein by reference in its entirety.

Figure 2:
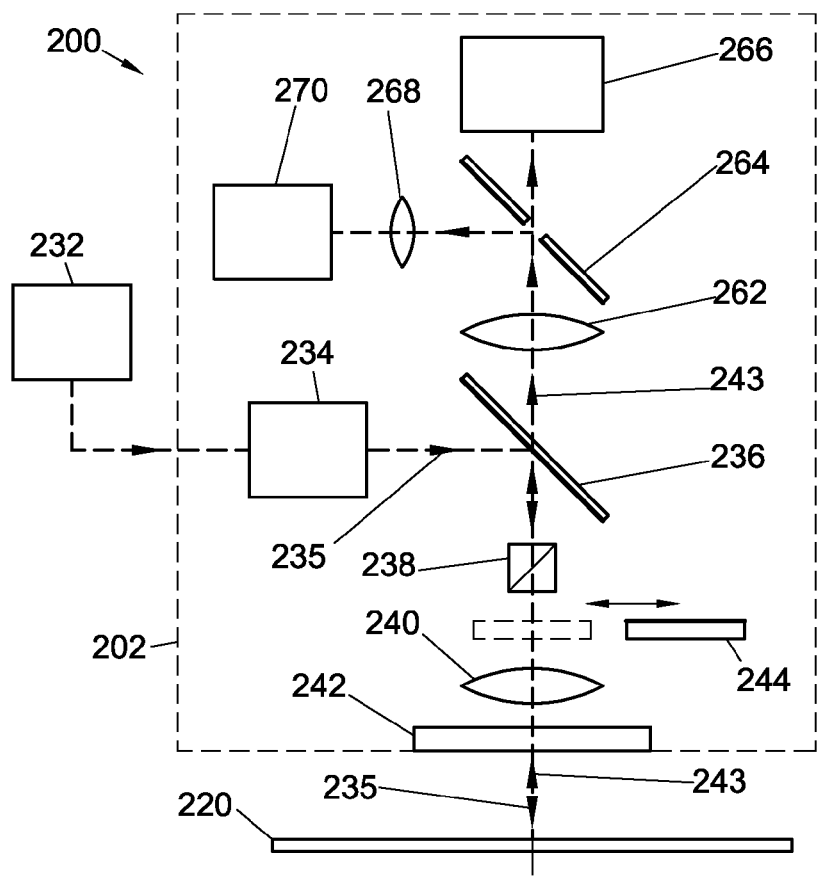
FIG. 2 is a schematic representation of an exemplary optical metrology system in accordance with an embodiment of the invention.

FIG. 2 is a schematic representation of an embodiment of optical metrology system 100 of FIG. 1. Optical metrology system 200 comprises a light source 232 whose output is directed via an optical fiber, or other suitable means such as a system of mirrors, to a collimator 234, comprising one or multiple lenses, which forms an illumination beam 235. The illumination beam 235 is reflected towards substrate 220 using a beam-splitter 236. An optional beam depolarizer 238 may be used to depolarize the illumination beam 235. The illumination beam 235 is thereafter directed into an objective lens assembly 240, which directs the axis of illumination beam 235 to be normal to the surface of substrate 220 (i.e. at a 0° angle of incidence), while at the same time focusing illumination beam 235 into a tight spot at the wafer surface. The size of the illuminated spot on substrate 220 can range from 10 to 200 μm. Objective lens assembly 240 may be implemented as either fully-reflective, i.e. using mirrors; or using lenses. The former implementation has the advantage of reducing light transmission losses, particularly in the UV and DUV parts of the spectrum. The reflected and diffracted detection beam 243 formed at the surface of substrate 220, is directed back through objective lens assembly 240, optional beam depolarizer 238, to the beam splitter 236, substantially re-tracing the path of illumination beam 235. Beam splitter 236 allows a portion of detection beam 243 to pass to the detection portion of optical metrology system 200. Inside the detection portion, an optional re-imaging lens system 262 may be used to re-focus the detection beam 243 onto the array detector of spectrometer 266, mounted behind a pinhole machined in mirror 264. A small field-of-view camera 270 and lens system 268 may optionally be used for metrology target structure acquisition and alignment prior to measuring diffraction signals.

Optical metrology system 200 may optionally comprise a movable mirror 244, capable of intercepting illumination beam 235 before it reaches the objective lens assembly 240, and sending the illumination beam 235 back towards spectrometer 266. During normal operation of optical metrology system 200 (i.e. when measuring diffraction signals), movable mirror 244 is kept in a position outside illumination beam 235. When positioned to intercept illumination beam 235, movable mirror 244 allows spectrometer 266 to make measurements of reference spectra of illumination beam 235, i.e. to determine the intensity of illumination beam 235 as a function of wavelength $\lambda$, which information may later be used to correct measured diffraction signals for spectral variations of illumination intensity.

With continuing reference to FIG. 2, a window 242 and enclosure 202 may optionally be used to protect optical metrology system 200 from contamination by the process environment of substrate 220. While FIG. 2 shows the light source 232 as being installed outside of optional enclosure 202, in an alternative embodiment the light source may be installed inside optional enclosure 202. Depending on contaminant levels in the environment in which optical metrology system 200 is operating, the optional enclosure 202 may be sealed and/or purged with a gas, such as an inert gas.

Figure 3:
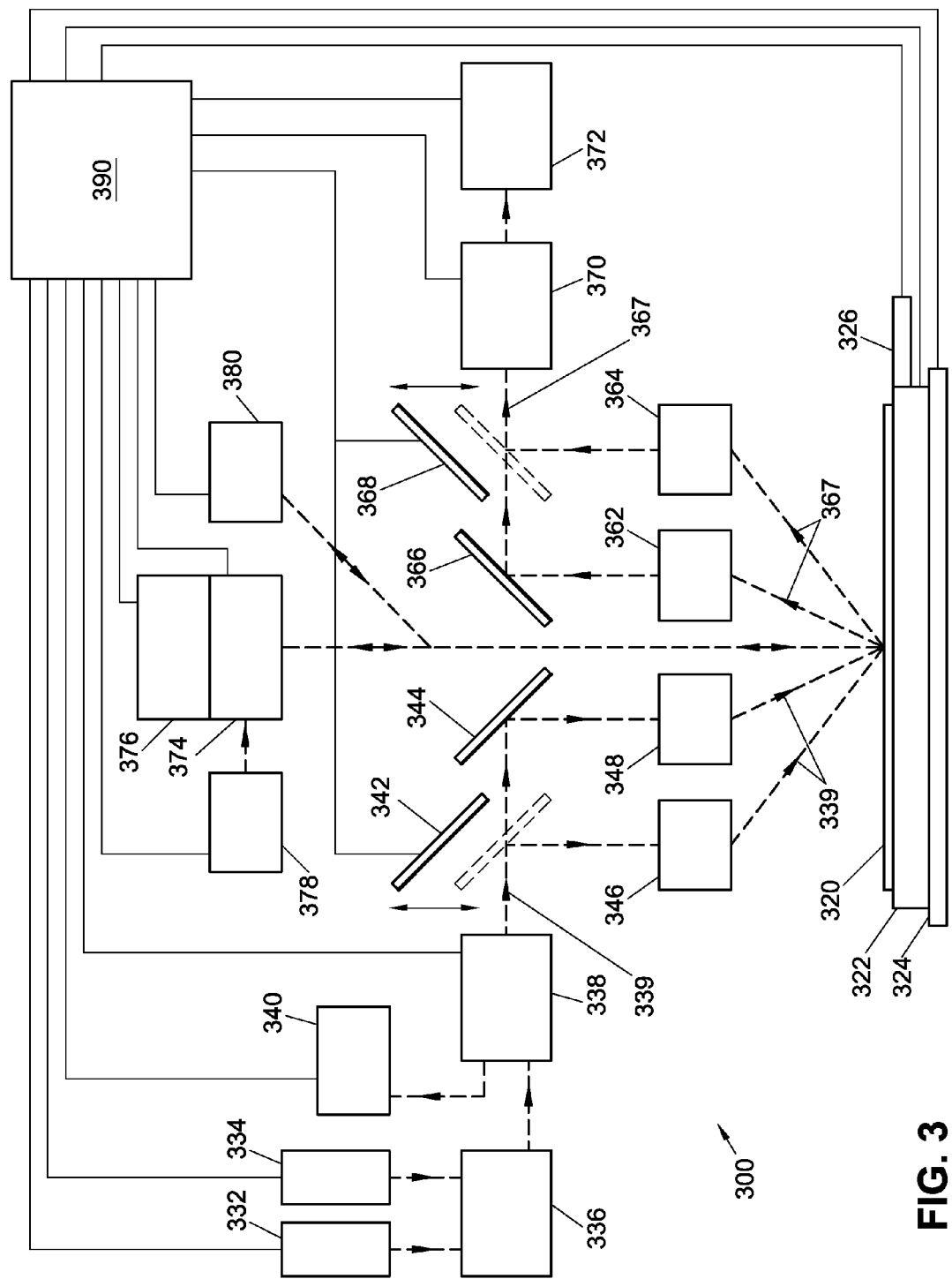
FIG. 3 is a schematic representation of another exemplary optical metrology system in accordance with an embodiment of the invention.

FIG. 3 shows another embodiment of optical metrology system 100 of FIG. 1. Optical metrology system 300 is configured to allow measuring diffraction signals at two different angles of incidence, and over a wide range of wavelengths from the near-infrared (NIR), down to the deep-ultraviolet (DUV). The wide range of measurable wavelengths is achieved by the use of at least two lamps which generate at least two illumination beams that illuminate the same spot on the substrate, and which are directed after reflection and diffraction to at least two spectrometers for detection of diffraction signals. This arrangement allows each of the components to be better optimized for the wavelength range that it covers. Light source 332 of optical metrology system 300 is comprised of at least two light sources. For example, in one embodiment, a deuterium ($D_2$) lamp may be used to provide light in the DUV and UV parts of the spectrum, while a xenon (Xe) lamp may be used for the near-UV, visible (VIS) and near-infrared (NIR) parts of the spectrum. The outputs of the at least two lamps comprising light source 332 are fed into beam selector 336, and from there into beam generator 338 which combines and collimates the outputs of the lamps of light source 332 into at least two illumination beams 339, to be used to illuminate a structure on substrate 320. The at least two illumination beams 339 may either have different wavelength ranges, or have different polarizations (e.g. s- or p-polarization, upon illuminating the substrate 320), or any combination thereof, as the metrology application demands. Beam selector 336 and beam generator 338 may utilize components such as beam homogenizers, lenses, mirrors, flip-in mirrors, and fixed or movable polarizers, to selectably form the at least two illumination beams 339. A portion of the illumination beams 339 may be directed onto an optional reference subsystem 340, which measures the integrated or wavelength-dependent intensities of illumination beams 339 to allow correction of measured diffraction signals for variations of lamp intensity over time. The system may further comprise a spectral calibration lamp 334, which can be used to facilitate wavelength calibrations of spectrometers 372 of the optical metrology system 300 when the beam generator 338 is configured to pass the lamp's output in place of illumination beams 339.

From beam generator 338, illumination beams 339 are fed into an illumination portion of an angle of incidence selector subsystem, comprising movable mirror 342 and fixed mirror 344. When positioned to intercept the incoming illumination beams 339 (position depicted by dashed lines), movable mirror 342 directs the illumination beams 339 to illuminate the substrate 320 at a high angle of incidence. If positioned not to intercept illumination beams 339, movable mirror 342 allows the at least two illumination beams 339 to proceed to fixed mirror 344 which directs the beams to illuminate substrate 320 at a low angle of incidence. In this fashion, measurements can be made of each metrology target structure located on substrate 320; at a high angle of incidence, and at a low angle of incidence, by simply moving movable mirror 342 into and outside of illumination beams 339. Combined with the capability of beam selector 336 and beam generator 338 to produce illumination beams 339 of various polarization orientations and wavelength ranges, this provides a versatile optical metrology system 300 adaptable to a wide range of metrology applications. Illumination beams 339 are focused into a tight illuminated spot on substrate 320 using a focusing subsystem comprised of focusing assemblies 346 and 348, for the high and low angle of incidence beam positions respectively. Focusing assemblies 346 and 348 may be implemented using lenses, or they may be implemented using reflective optics, such as mirrors. In one embodiment, focusing assemblies 346 and 348 (and also focusing assemblies 362 and 364 on the detection side) may be parts of a single focusing assembly in which high and low angle of incidence beams follow different paths through the assembly which may, for example, be configured as a Schwarzschild or modified Schwarzschild all-reflective objective lens. In addition to focusing the individual illumination beams 339 so they illuminate spots of size ranging from 10 to 200 µm, at the substrate, the assemblies also direct the at least two illumination beams 339 to illuminate substantially the same spot on substrate 320 even though the illumination beams 339 propagate along different paths throughout optical metrology system 300 before reaching the metrology target structure.

Simpler alternative embodiments of optical metrology system 300 may omit movable mirror 342 and focusing assembly 346, to provide a single angle of incidence optical metrology system. To provide more flexibility in setting an angle of incidence, other alternative embodiments may employ three or more angles of incidence, simply by including additional movable mirrors similar to movable mirror 342, to allow directing of illumination beams 339 at substrate 320 at angles of incidence other than those defined by movable mirror 342 and fixed mirror 344. Other alternative embodiments may employ a single illumination beam 339 instead of at least two illumination beams 339. Furthermore, yet other alternative embodiments may employ illumination beams 339 that are depolarized, as in optical metrology system 200 of FIG. 2, instead of being polarized. Alternatively, the polarization orientation of illumination beams 339 may be caused to rotate at an angular velocity ω, e.g. by spinning polarizers internal to beam generator 338, to allow the optical metrology system to be used as a multi-beam ellipsometer. Alternatively yet, the polarization orientation of illumination beams 339 can be made to vary among a set of fixed polarization orientations, which would allow diffraction signal measurements to be made at different fixed polarization orientations, from the same metrology target structure.

Upon reflection and diffraction from the target structure on substrate 320, the at least two illumination beams 339 form at least two detection beams 367 carrying their respective diffraction signals. Focusing assemblies 362 and 364 are used for focusing of detection beams 367 and sending them into the detection portion of the angle of incidence selector subsystem, comprising movable mirror 368 and fixed mirror 366. Movable mirror 368 is operated in conjunction with movable mirror 342, such that when a high angle of incidence is selected using movable mirror 342, movable mirror 368 is positioned to intercept the at least two high angle of incidence detection beams 367, and send them towards an analyzer subsystem 370. Analyzer subsystem 370 may comprise, for example, fixed or movable polarizers, which can serve to select polarization orientations of the at least two detection beams 367, to be detected by the at least two spectrometers 372. For example, the polarizers may be used to select the s- or p-polarization orientation in conjunction with the polarization setting of beam generator 338. In an alternative embodiment, analyzer subsystem 370 may comprise polarizers rotating at angular velocity ω, to allow the optical metrology system 300 to operate as a multi-beam ellipsometer. Alternatively yet, the analyzer subsystem 370 may comprise polarizers which can be positioned among a fixed set of polarization orientations, to complement a similar capability of beam generator 338. The analyzer subsystem 370 may further comprise lenses and pinholes to re-focus the at least two detection beams 367 onto the at least two spectrometers 372. Depending on the configuration of beam generator 338 and analyzer subsystem 370, individual spectrometers 372 may serve to detect different wavelength ranges, or different polarizations, etc. Detection beams are focused onto detector arrays of spectrometers 372, which measure diffraction signals and convert them into electrical signals to be transmitted to processor 390 for comparison against simulated diffraction signals.

The substrate 320 is placed on XYZΘ stage 322, which provides substrate position feedback to processor 390 via alignment sensor 326. The entire XYZΘ stage 322 is mounted atop platform base 324. The X, Y, and Θ motions of stage 322 are used to align the illuminated spot onto a metrology target structure for measurement, and the Z motion is used to bring the substrate and metrology target structure into focus. In an alternative embodiment, the substrate can be placed on a fixed stage 322, and the entire optical metrology system 300 may be mounted on a moveable stage (not shown), to facilitate alignment and focusing. Alternatively yet, stage 322 may allow only Z motion, while the optical metrology system 300 is mounted on a moveable stage (not shown) that performs the remaining alignment motions (i.e. X, Y, and possibly Θ).

Optical metrology system 300 may further comprise an autofocusing subsystem 380, which determines if the metrology target structure has been brought into sharp focus via Z motion of stage 322, and provides motion instructions to stage 322 via processor 390 until sharp focus is achieved. An illumination subsystem 378 comprising one or more light sources is used to illuminate substrate 320 during the metrology target structure alignment phase, and a small field-of-view camera 376 and imaging subsystem (e.g. lens) 374 are used to provide metrology target structure location information to processor 390, such that stage 322 can be operated to bring the desired metrology target structure exactly underneath the illuminated spot created by the at least two illumination beams 339.

In addition to acquisition and comparison of diffraction signals with simulated diffraction signals, and controlling the position of stage 322, processor 390 further serves to control the various other subsystems and components of optical metrology system 300, such as light source 332, calibration light source 334, optional reference subsystem 340, beam selector 336, beam generator 338, analyzer subsystem 370, spectrometers 372, movable mirrors 342 and 368, etc. Processor 390, which may be implemented as a general purpose computer, and may include a processor, memory, I/O channels, fixed and removable storage devices, a graphical user interface, etc., is configured to receive metrology process instructions (i.e. a recipe) from, for example, the user, or another computer over a local network, intranet, or across the Internet. It may be configured to communicate acquired metrology and recipe-related data to the user, or to other computers over a local network, intranet, or across the Internet.

Figure 4:
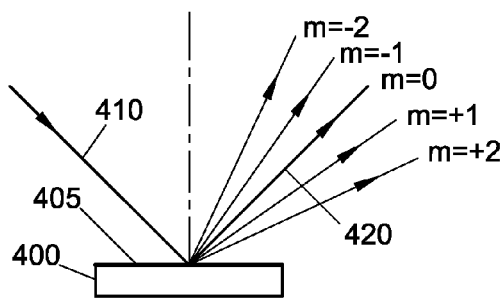
FIG. 4 is a schematic representation of a diffraction grating with diffraction orders produced, and their spatial, i.e. angular relationship.

FIG. 4 shows a diffraction grating 400 typically employed by spectrometers in optical metrology systems. The grating front surface 405 is blazed, ruled, or scribed, using mechanical, photolithographic, or holographic techniques. An incident beam 410 is dispersed by the diffraction grating 400 into a plurality of diffraction orders 420, of which order m=0 represents a specular reflection, and is not particularly useful as the incident beam 410 is not dispersed in that order. Of the nonzero diffraction orders, orders m=+1 and m=−1 are usually the strongest, and also fully dispersed, and therefore one is typically measured by an array detector in optical metrology systems. If the bandwidth of incident beam 410 does not exceed one octave, the diffraction orders 420 will not overlap in angle. However, if the bandwidth of the incident beam exceeds an octave, as is typically the case in optical metrology systems, then diffraction orders begin to overlap in angle. In this case, an array detector pixel may measure, in addition to the first diffraction order of calibrated wavelength $\lambda$, the second diffraction order of wavelength $\lambda/2$, and if the signal bandwidth exceeds two octaves, also the third diffraction order of wavelength $\lambda/3$. This undesirable situation is avoided by utilizing an order sorting filter (OSF).

Figure 5:
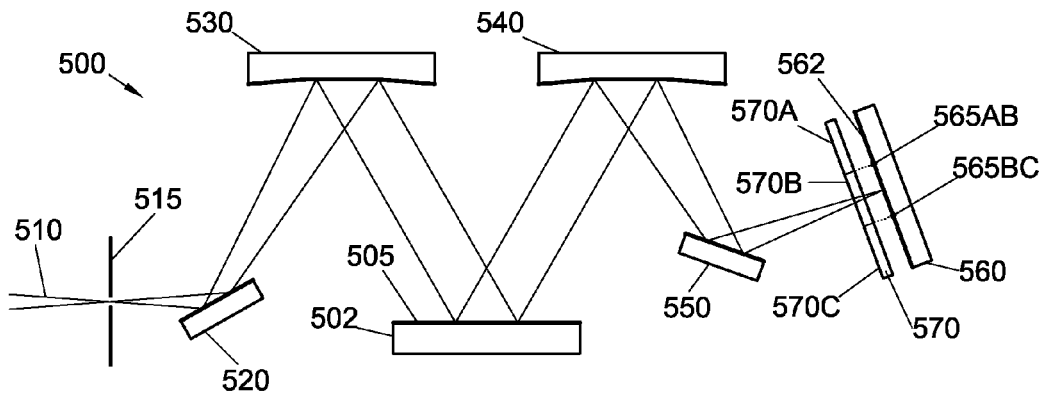
FIG. 5 is a schematic representation of an exemplary spectrometer suitable for a semiconductor optical metrology system, in accordance with an embodiment of the invention.
Figure 16:
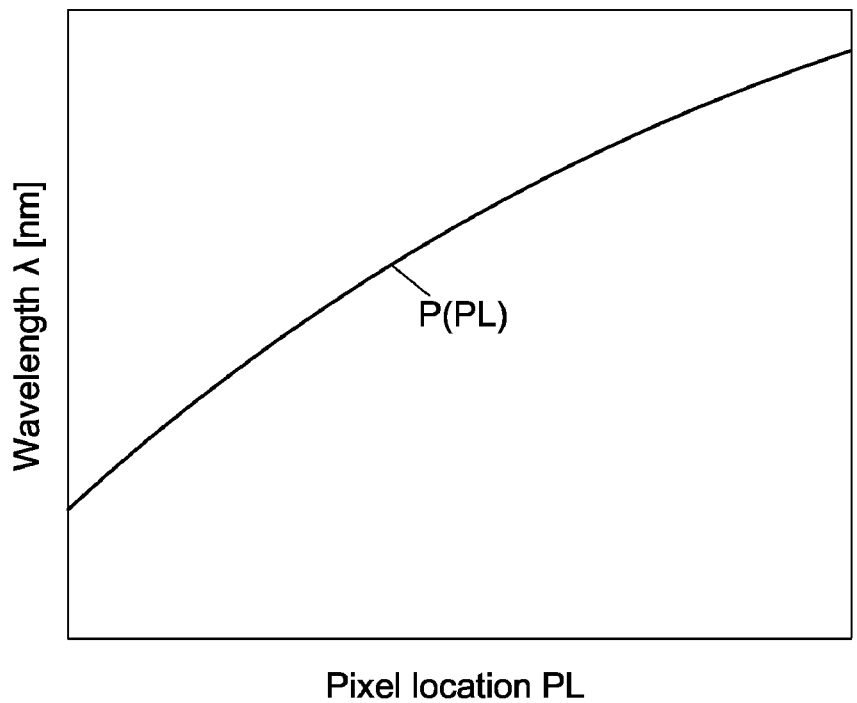
FIG. 16 is a graph of an exemplary wavelength to pixel location calibration curve fit.

FIG. 5 shows a schematic of an embodiment of spectrometer 266 of FIG. 2, or one of at least two spectrometers 372 of FIG. 3. In spectrometer 500, the incident beam 510 is focused at an imaging pinhole or slot 515, and after being reflected by mirrors 520 and 530, it reaches the blazed or ruled front surface 505 of diffraction grating 502. The incident beam 510, now dispersed, is directed using mirrors 540 and 550 onto array detector 560, which may be a photodiode array, a focal plane array, a CCD detector, a CMOS detector, or the like. In the array detector, incoming light intensities of different wavelengths of incident beam 510, dispersed by diffraction grating 502, are converted into electrical outputs which can be further digitally processed by, for example, processors 180 and 390 of FIGS. 1 and 3, respectively. Pixels of array detector 560 are typically arranged in a linear fashion along the light sensitive surface 562, each pixel receiving and measuring the intensity of a different wavelength $\lambda$ of the dispersed incident beam 510. To calibrate the pixel locations to actual wavelengths $\lambda$ of the incident beam 510, a spectral calibration lamp may be used to generate an incident beam 510 with precisely known spectral components that can be used to establish a wavelength to pixel location (i.e. pixel number) calibration curve, usually expressed as a $3^{rd}$ or $4^{th}$ order polynomial, an example of which is shown in FIG. 16. The optical design of the spectrometer 500 affects the wavelength to pixel location calibration curve, which is typically linear or slightly quadratic in contemporary spectrometer designs over the entire wavelength range from near-infrared (NIR) to the deep ultraviolet (DUV). Depending on the spectrometer configuration, mirrors 520, 530, 540, and 550 may be either flat or curved (convex or concave), and the diffraction grating 502 may also be flat or curved (convex or concave). In the exemplary embodiment of FIG. 4, the spectrometer employs a flat diffraction grating 502 and mirrors 520 and 550, and concave mirrors 530 and 540.

Before reaching the light sensitive surface 562 of array detector 560, incident beam 510 is transmitted through order sorting filter (OSF) 570, mounted parallel to and in close proximity to (e.g. a few millimeters away from) the array detector 560, and also substantially perpendicular to incident beam 510. In alternative embodiments, the OSF 570 may be mounted in a position that is not parallel to array detector 560, and/or not perpendicular to incident beam 510, the latter modification having the benefit of preventing light reflections from the OSF from re-tracing along the path of incident beam 510 towards diffraction grating 502. In the embodiment of FIG. 4, a zoned OSF with three filter zones 570A, 570B, and 570C is used, but alternative embodiments, particularly for spectrometers of high bandwidth, may employ more than three zones. Alternatively, if the bandwidth of the spectrometer is lower, an OSF may employ only two zones. Further discussion of the OSF 570 will assume a three-zone OSF, but it is understood that all inventive concepts may be extended to OSF 570 with two zones, or more than three zones.

The three filter zones 570A, 570B, and 570C each act as long-pass or band-pass filters to ensure that pixels of array detector 560, located immediately underneath the respective filter zones, do not receive any light from diffraction orders higher than the measured diffraction order (typically one of the first orders, m=±1). In most cases, OSF 570 is built on a common optically-transparent substrate, such as a piece of DUV grade silica, and the filter zones 570A, 570B, and 570C are formed as thin-film stack filters atop the optically-transparent substrate. Antireflection coatings may be applied to the OSF surface opposite the filter zone thin-film stacks. Ideally, thin-film stack filters of filter zones 570A, 570B, and 570C do not overlap each other. However, manufacturing tolerances usually allow a certain amount of overlap or a slight gap at the zone joints. Varying passbands of the individual filter zones 570A, 570B, and 570C result in varying optical lengths that the incident beam 510 traverses across filter zones 570A, 570B, and 570C. The inventors have discovered that the sudden change of traversed optical length at the zone joints, combined with manufacturing imperfections of zone joints mentioned before, may give rise to anomalies in measured spectra at or in the vicinity of pixels 565AB and 565BC located at places where zone joints between filter zones 570A and 570B, and 570B and 570C, respectively, are projected onto light sensitive surface 562 of array detector 560, along the path of incident beam 510. These anomalies manifest themselves as localized nonlinearities of the wavelength to pixel location calibration curve, and are caused by unwanted dispersion of the incident beam 510 at the zone joint. Unwanted dispersion can cause the beam incident on the zone joint to spread over multiple pixels surrounding pixels 565AB and 565BC of array detector 560, and/or to completely shift the beam image centroid away from pixels 565AB and 565BC.

Figure 6:
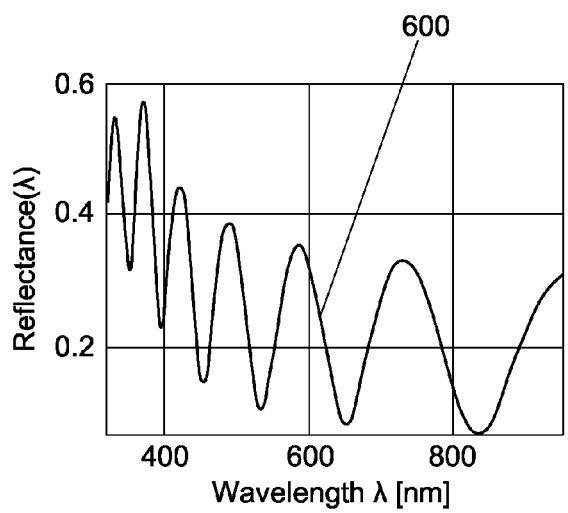
FIG. 6 is an exemplary graph of reflectance vs. wavelength, i.e. a diffraction signal, of a smooth $SiO_2$ film on a silicon surface, measured by an optical metrology system.

Wavelength to pixel location calibration may be combined with array detector intensity readout calibration, and both calibrations can be performed together in an iterative process using multiple samples of known reflectance as input. In this process, the samples would be placed in, for example, the optical metrology system 100 of FIG. 1, in place of semiconductor substrate 120, and measurements of diffraction signals, i.e. intensity vs. pixel location would be taken by the spectrometer inside metrology beam receiver 160. These measured diffraction signals are then utilized in an iterative refinement calibration process where, for example, a linear polynomial fit is made to the array detector pixel intensity readouts, i.e. for intensity calibration; and $3^{rd}$ or $4^{th}$ order polynomial fits are made to the wavelength vs. pixel location data (an example wavelength to pixel location calibration curve is shown in FIG. 16). Alternatively, other polynomial orders may be used for the intensity and/or wavelength calibrations, or one or both calibrations may employ mathematical functions other than polynomials. In one embodiment of the calibration process, a single data set for intensity calibration may be used, such as for example, data on reflectance of polished bare silicon substrates, and multiple data sets may be used for wavelength to pixel location calibration, such as for example, data on reflectance of $SiO_2$-coated silicon substrates, where the $SiO_2$ thickness varies in the samples. Alternatively, the numbers of samples used for the intensity and wavelength calibration may be different than above, e.g. more than one sample may be used for intensity calibration. FIG. 6 shows an exemplary graph 600 of reflectance vs. wavelength for a silicon substrate with a 999 nm thick $SiO_2$ film deposited on its top surface, measured at zero angle of incidence θ, i.e. normal incidence. In one exemplary embodiment, the wavelength calibration process may employ five samples with different $SiO_2$ film thickness, for example 51.81 nm, 102.5 nm, 197.8 nm, 399 nm, and 999 nm. The calibration process proceeds by alternately refining the polynomial fit coefficients for the linear intensity calibration, and $3^{rd}$ or $4^{th}$ order polynomial fit coefficients for the wavelength to pixel location calibration, using the RMS (root mean square) value of reflectance residual $R(\lambda)$ as a criterion for calibration convergence and termination, i.e. as a goodness of fit measure. The reflectance residual $R(\lambda)$ is defined as the difference between the known sample reflectance and measured reflectance determined using the most recent set of calibration polynomial fit coefficients, at a given wavelength λ. The RMS reflectance residual is simply the root mean square (RMS) variation of the reflectance residual $R(\lambda)$ calculated over the entire range of wavelengths measured by the array detector. Typically, the polynomial fit coefficients and the RMS reflectance residual change rapidly in the first few iterations, and the calibration process terminates when there is no further improvement of the RMS reflectance residual, and the final polynomial fit coefficients are used for calculations of intensity readouts of pixels of the array detector, and to convert pixel locations into wavelengths.

Figure 7:
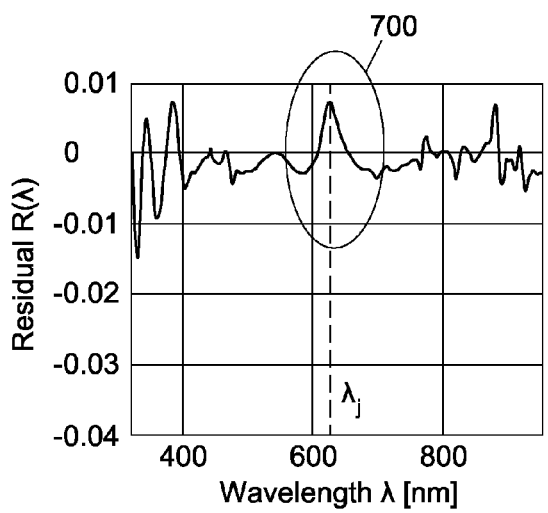
FIG. 7 is an exemplary graph of reflectance residual vs. wavelength, resulting from an iterative spectrometer calibration process using a sample of known reflectance.

FIG. 7 shows an exemplary graph of reflectance residual $R(\lambda)$ vs. wavelength λ upon completion of the iterative calibration process, for the same sample whose reflectance was plotted in FIG. 6. In this example, a peak 700 of the reflectance residual $R(\lambda)$ is immediately apparent at wavelength $\lambda_j$ that corresponds to a zone joint in the order sorting filter (OSF) of the optical metrology system used to acquire the diffraction signal. As the inventors have discovered, further iterative refinement of the polynomial fit coefficients for the wavelength to pixel location calibration would not result in a reduction of the $R(\lambda)$ peak 700 because of the highly nonlinear nature of the calibration curve in the vicinity of the OSF zone joint. This localized nonlinearity which is caused by dispersion at the zone joint due to unequal traversed optical lengths across zones adjacent the zone joint, and/or overlaps or gaps between the zones, cannot be captured and represented accurately using a $3^{rd}$ or $4^{th}$ order calibration polynomial that applies to all pixel locations of the array detector, and across all zones and zone joints of the OSF.

However, as the inventors have discovered, at least the unequal traversed optical lengths of the OSF zones can be corrected using suitably located underlayers that are made of such thickness that the total traversed optical lengths of zones adjacent a zone joint are made substantially equal, thus minimizing unwanted dispersion of the measured diffraction order, at the zone joint. Matching optical lengths across zones is sometimes not practical, and an alternative which achieves the same effect is substantially matching the phase of emerging beams of the measured diffraction order, from the zones adjacent the zone joint. In the latter case, the traversed optical length can vary from one zone to another, across the zone joint, but to achieve a phase match, the traversed optical lengths have to differ by an integer number of full wavelengths $\lambda_j$, incident at the zone joint. Keeping the emerging beams substantially in phase across the zone joint, as opposed to substantially matching the traversed optical lengths, also minimizes dispersion at the joint, while providing some flexibility in the choice of underlayer thicknesses, which may be advantageous in the OSF manufacturing process. The first requirement of matching traversed optical lengths is only a special case of the phase matching requirement wherein the difference of traversed optical lengths is zero wavelengths $\lambda_j$. For the purpose of this disclosure, substantially matching the phase of two emerging beams from zones adjacent a zone joint means that the phases of these two beams differ by a specified tolerance, sufficient to reduce or entirely remove the peak of reflectance residual $R(\lambda)$ (for example, peak 700 of FIG. 7), due to a reduction of dispersion at the zone joint, as compared to other fluctuations of the reflectance residual $R(\lambda)$. The tolerance for beam phase matching may vary from 0 to 60°, or alternatively from 0 to 45°, or alternatively yet from 0 to 30°, depending on the criticality of the application Similarly, for the purpose of this disclosure, substantially matching the traversed optical length of two emerging beams from zones adjacent a zone joint means that the traversed optical lengths of these two beams differ by a specified tolerance, sufficient to reduce or entirely remove the peak of reflectance residual $R(\lambda)$ (for example, peak 700 of FIG. 7), due to a reduction of dispersion at the zone joint, as compared to other fluctuations of the reflectance residual $R(\lambda)$. The tolerance for beam traversed optical length matching is typically expressed in terms of the wavelength of light incident upon the zone joint, and can vary from 0 to $\lambda/6$, or alternatively from 0 to $\lambda/8$, or alternatively yet from 0 to $\lambda/12$, depending on the criticality of the application. In this disclosure, the terms "matching" and "substantially matching", and "equal" and "substantially equal" are used interchangeably when discussing phase-matching and traversed optical length matching across a zone joint, because an exact match is not usually attainable, and it is the match tolerance that controls the reduction of and elimination of the peak of reflectance residual $R(\lambda)$. Furthermore, matching either the phase or optical path length across the zone joint can only be achieved for a relatively narrow range of wavelengths λ that fall near the zone joint, and for the purpose of further discussion, whenever it is said that traversed optical lengths are matched, or phases are matched across a zone joint, it will be understood that the matching condition applies only to the measured diffraction order, unless stated otherwise. Lastly, matching the optical path lengths, as compared to matching the phase, will allow for a wider range of wavelengths to substantially match, in the vicinity of the zone joint, and can help relax positioning tolerances of the filter.

Figure 8:
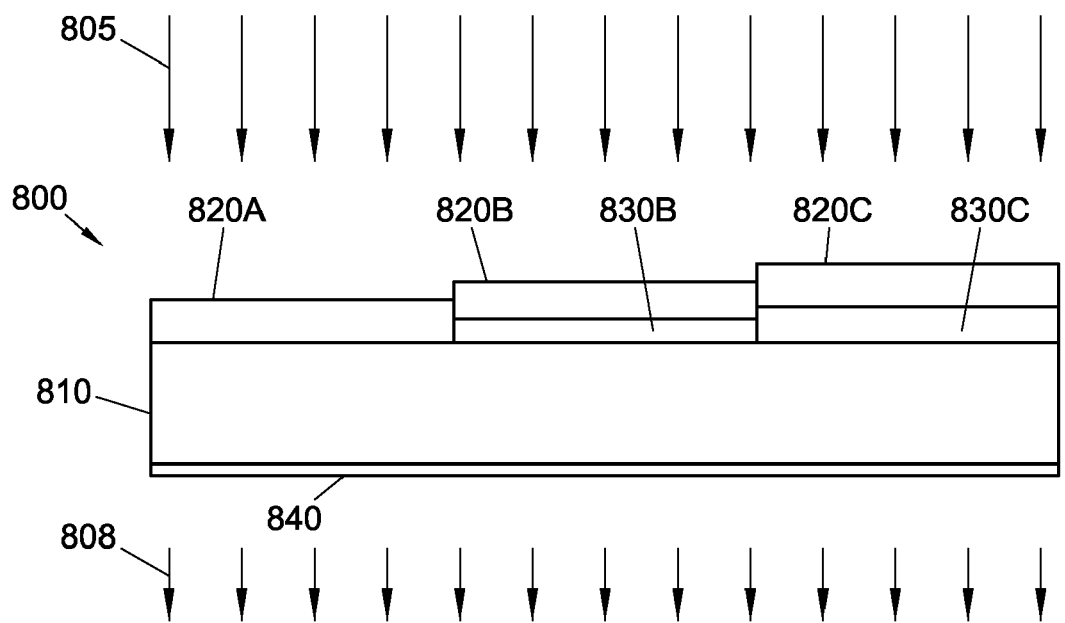
FIG. 8 is a schematic representation of a diffraction order sorting filter in accordance with an embodiment of the invention.

FIG. 8 shows an embodiment 800 of, for example, order sorting filter (OSF) 570 of FIG. 5. OSF 800 has three zones, whose passbands are determined by thin-film stack filters 820A, 820B, and 820C respectively, all deposited on a common optically-transparent substrate 810. The optically-transparent substrate 810 can be made of DUV grade silica, to allow for high transmission in the UV and DUV parts of the spectrum, but other materials can also be used, such as various types of glass, quartz, calcium-fluoride, sapphire, etc. An antireflective coating 840 may be applied to the side of optically-transparent substrate opposite the thin-film stack filters 820A, 820B, and 820C, to minimize light reflections at the substrate-to-air interface. Thin-film stack filters 820A, 820B, and 820C are made of multiple thin films, whose thicknesses and materials determine their passband.

The process of designing thin-film stack filters given a set of known passband requirements and other constraints is well known in the optical arts, and will not be further discussed herein, in connection with this or any of the embodiments to follow.

Incident light beam 805 is transmitted through thin-film stack filters 820A, 820B, 820C, the optically-transparent substrate 810, and the optional antireflective coating 840, to form the transmitted beam 808. Incident beam 805 and transmitted beam 808 may propagate perpendicular to the surface of OSF 800, as is shown in FIG. 8, or they may propagate at angles not normal with respect to the surface of OSF 800, as the spectrometer design and mounting angles of the OSF may dictate. As mentioned before, in a prior art OSF, the optical length traversed by incident beam 805 across the entire OSF 800 will vary from one zone to another, causing dispersion at the zone joints and the emergence of transmitted beam 808 that underwent different phase changes while traversing the two zones adjacent a zone joint. To correct this, underlayers 830B and 830C are deposited on optically-transparent substrate 810 before the deposition of thin-film stack filters 820A, 820B, and 820C respectively. To reduce internal reflections at the interface between the underlayers 830B, 830C, and the optically-transparent substrate 810, underlayers 830B and 830C must be made of a material with substantially the same index of refraction as that of optically-transparent substrate 810. For example, if the material of the optically-transparent substrate 810 is DUV grade silica, then underlayers 830B and 830C may be formed of $SiO_2$ which has substantially the same index of refraction.

To minimize dispersion at the zone joint between thin-film stack filters 820A and 820B, the thickness of underlayer 830B is adjusted such that the traversed optical length across thin-film stack filter 820B and underlayer 830B, is equal to the traversed optical length across only thin-film stack filter 820A of the adjacent zone. Alternatively, as explained before, the requirement for phase matching of emerging beams at the zone joint may be satisfied by making the thickness of underlayer 830B such that the traversed optical length of wavelength $\lambda_j$ incident at the zone joint, across thin-film stack filter 820B and underlayer 830B, differs from the traversed optical length across only thin-film stack filter 820A of the adjacent zone, by an integer number of wavelengths $\lambda_j$. In similar vein, to minimize dispersion at the zone joint between thin-film stack filters 820B and 820C, the thicknesses of underlayers 830B and 830C are adjusted such that the traversed optical length across thin-film stack filter 820C and underlayer 830C, is equal to the traversed optical length across thin-film stack filter 820B and underlayer 830B, of the adjacent zone. Alternatively, the requirement for phase matching of emerging beams at the zone joint may be satisfied by making the thicknesses of underlayers 830B and 830C such that the traversed optical length of wavelength $\lambda_j$ incident at the zone joint, across thin-film stack filter 820C and underlayer 830C, differs from the traversed optical length across thin-film stack filter 820B and underlayer 830B, of the adjacent zone, by an integer number of wavelengths $\lambda_j$. In this fashion, the transmitted beam 808 emerges from all OSF zones "in phase" across zone joints, and dispersion at the zone joints is minimized. In determining the thicknesses of underlayers 830B and 830C, the angle of incidence of incident beam 805 needs to be taken into account, as it affects the traversed optical lengths.

The OSF zone with thin-film stack filter 820A, which lacks an underlayer, has high light transmission, and can be used, for example, for the UV and DUV part of the spectrum, where transmission losses are high and signal levels low in typical optical metrology systems. The remaining zones can be used for near ultraviolet, visible (VIS) and near-infrared (NIR) parts of the spectrum, where transmission losses and signal levels present less of a concern.

Figure 9:
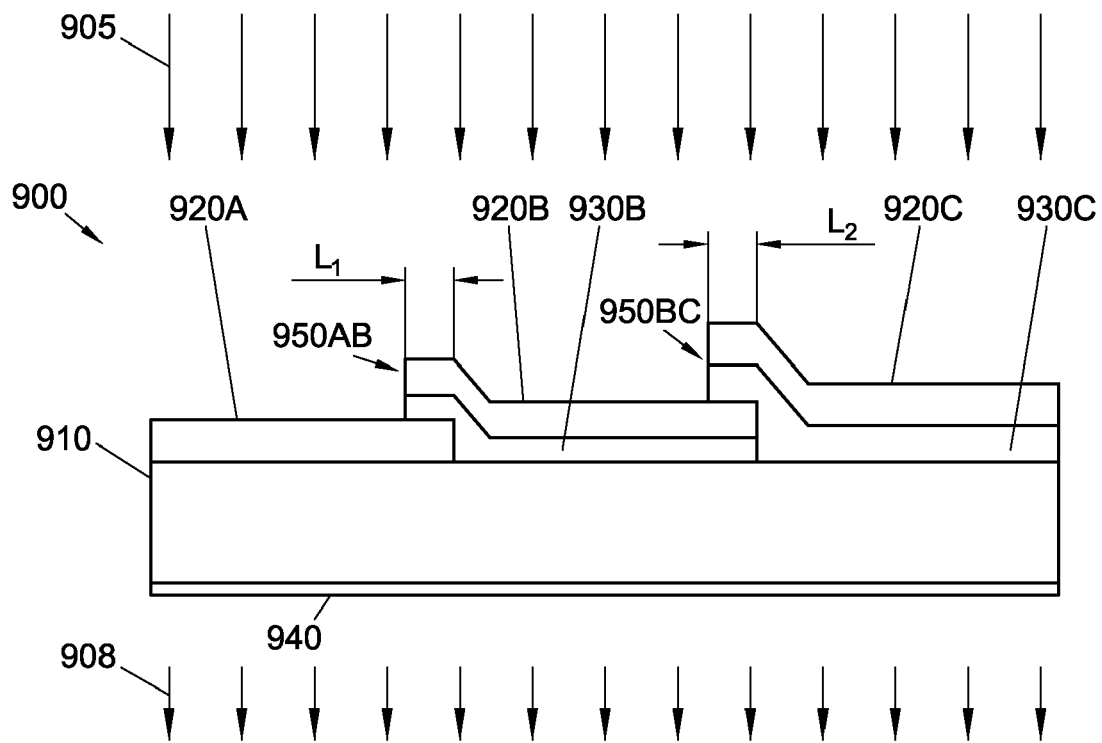
FIG. 9 is a schematic representation of a diffraction order sorting filter in accordance with an embodiment of the invention.

FIG. 9 shows an embodiment 900 of, for example, order sorting filter (OSF) 570 of FIG. 5. OSF 900 has three zones, whose passbands are determined by thin-film stack filters 920A, 920B, and 920C respectively, all deposited on a common optically-transparent substrate 910. The optically-transparent substrate 910 can be made of DUV grade silica, to allow for high transmission in the UV and DUV parts of the spectrum, but other materials can also be used, such as various types of glass, quartz, calcium-fluoride, sapphire, etc. An antireflective coating 940 may be applied to the side of optically-transparent substrate opposite the thin-film stack filters 920A, 920B, and 920C, to minimize light reflections at the substrate-to-air interface. Thin-film stack filters 920A, 920B, and 920C are made of multiple thin films, whose thicknesses and materials determine their passband.

Incident light beam 905 is transmitted through thin-film stack filters 920A, 920B, 920C, the optically-transparent substrate 910, and the optional antireflective coating 940, to form the transmitted beam 908. Incident beam 905 and transmitted beam 908 may propagate perpendicular to the surface of OSF 900, as is shown in FIG. 9, or they may propagate at angles not normal with respect to the surface of OSF 900, as the spectrometer design and mounting angles of the OSF may dictate. As mentioned before, in a prior art OSF, the optical length traversed by incident beam 905 across the entire OSF 900 will vary from one zone to another, causing dispersion at the zone joints and the emergence of transmitted beam 908 that underwent different phase changes while traversing the two zones adjacent a zone joint. To correct this, underlayers 930B and 930C are deposited on optically-transparent substrate 910 before the deposition of thin-film stack filters 920A, 920B, and 920C respectively. To reduce internal reflections at the interface between the underlayers 930B, 930C, and the optically-transparent substrate 910, underlayers 930B and 930C must be made of a material with substantially the same index of refraction as that of optically-transparent substrate 910. For example, if the material of the optically-transparent substrate 910 is DUV grade silica, then underlayers 930B and 930C may be formed of $SiO_2$ which has substantially the same index of refraction.

To minimize dispersion at the zone joint between thin-film stack filters 920A and 920B, the thickness of underlayer 930B is adjusted such that the traversed optical length across thin-film stack filter 920B and underlayer 930B, is equal to the traversed optical length across only thin-film stack filter 920A of the adjacent zone. Alternatively, as explained before, the requirement for phase matching of emerging beams at the zone joint may be satisfied by making the thickness of underlayer 930B such that the traversed optical length of wavelength $\lambda_j$ incident at the zone joint, across thin-film stack filter 920B and underlayer 930B, differs from the traversed optical length across only thin-film stack filter 920A of the adjacent zone, by an integer number of wavelengths $\lambda_j$. In similar vein, to minimize dispersion at the zone joint between thin-film stack filters 920B and 920C, the thicknesses of underlayers 930B and 930C are adjusted such that the traversed optical length across thin-film stack filter 920C and underlayer 930C, is equal to the traversed optical length across thin-film stack filter 920B and underlayer 930B, of the adjacent zone. Alternatively, the requirement for phase matching of emerging beams at the zone joint may be satisfied by making the thicknesses of underlayers 930B and 930C such that the traversed optical length of wavelength $\lambda_j$ incident at the zone joint, across thin-film stack filter 920C and underlayer 930C, differs from the traversed optical length across thin-film stack filter 920B and underlayer 930B, of the adjacent zone, by an integer number of wavelengths $\lambda_j$. In this fashion, the transmitted beam 908 emerges from all OSF zones "in phase" across zone joints, and dispersion at the zone joints is minimized. In determining the thicknesses of underlayers 930B and 930C, the angle of incidence of incident beam 905 needs to be taken into account, as it affects the traversed optical lengths.

Unlike OSF 800 of FIG. 8, OSF 900 of FIG. 9 is manufactured with somewhat relaxed manufacturing tolerances, which allow the formation of overlaps 950AB and 950BC, atop of the zone joints. In these overlaps, both an underlayer and a thin-film stack filter are allowed to overlap an adjacent zone in which the underlayer and/or thin-film stack filter have already been deposited. The widths of overlaps 950AB and 950BC, $L_1$ and $L_2$ respectively, can vary, for example, from 0 to 400 μm, or alternatively from 0 to 200 μm. Depending on the OSF manufacturing process, tolerances may also allow the formation of gaps between zones, instead of overlaps 950AB and 950BC. Also, the OSF zone with thin-film stack filter 920A, which lacks an underlayer, has high light transmission, and can be used, for example, for the UV and DUV part of the spectrum, where transmission losses are high and signal levels low in typical optical metrology systems. The remaining zones can be used for near ultraviolet, visible (VIS) and near-infrared (NIR) parts of the spectrum, where transmission losses and signal levels present less of a concern.

Figure 10:
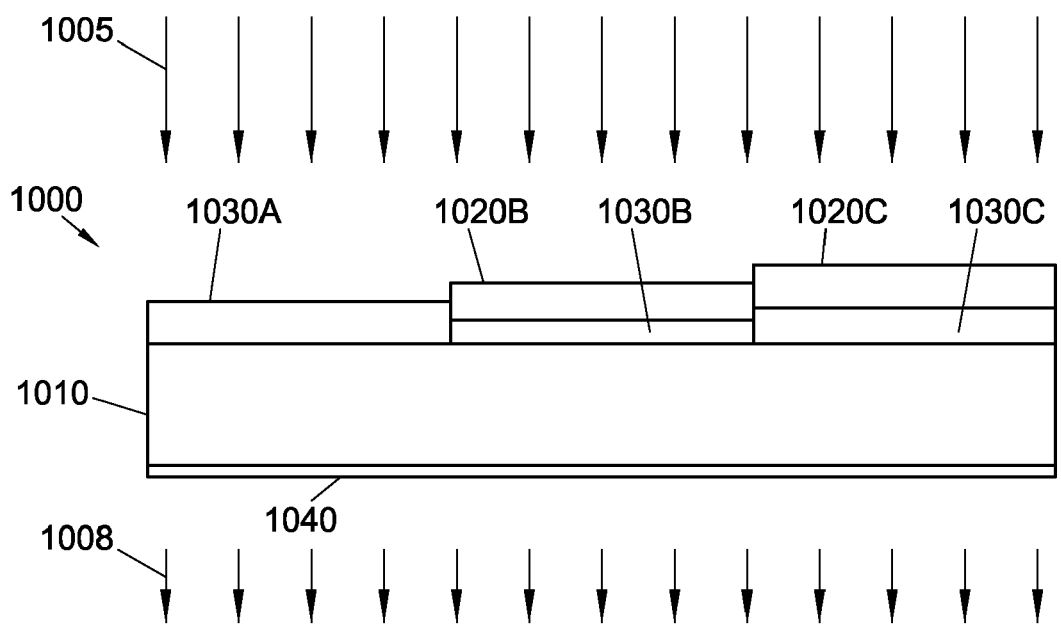
FIG. 10 is a schematic representation of a diffraction order sorting filter in accordance with another embodiment of the invention.

FIG. 10 shows an embodiment 1000 of, for example, order sorting filter (OSF) 570 of FIG. 5. OSF 1000 has three zones, of which the first one does not have a thin-film stack filter deposited thereupon. The passbands of the remaining two zones are determined by thin-film stack filters 1020B and 1020C respectively, all deposited on a common optically-transparent substrate 1010. The optically-transparent substrate 1010 can be made of DUV grade silica, to allow for high transmission in the UV and DUV parts of the spectrum, but other materials can also be used, such as various types of glass, quartz, calcium-fluoride, sapphire, etc. An antireflective coating 1040 may be applied to the side of optically-transparent substrate opposite the thin-film stack filters 1020B and 1020C, to minimize light reflections at the substrate-to-air interface. Thin-film stack filters 1020B and 1020C are made of multiple thin films, whose thicknesses and materials determine their passband.

Incident light beam 1005 is transmitted through thin-film stack filters 1020B and 1020C, the optically-transparent substrate 1010, and the optional antireflective coating 1040, to form the transmitted beam 1008. Incident beam 1005 and transmitted beam 1008 may propagate perpendicular to the surface of OSF 1000, as is shown in FIG. 10, or they may propagate at angles not normal with respect to the surface of OSF 1000, as the spectrometer design and mounting angles of the OSF may dictate. As mentioned before, in a prior art OSF, the optical length traversed by incident beam 1005 across the entire OSF 1000 will vary from one zone to another, causing dispersion at the zone joints and the emergence of transmitted beam 1008 that underwent different phase changes while traversing the two zones adjacent a zone joint. To correct this, underlayers 1030A, 1030B, and 1030C are deposited on optically-transparent substrate 1010 before the deposition of thin-film stack filters 1020B and 1020C respectively. To reduce internal reflections at the interface between the underlayers 1030A, 1030B, and 1030C, and the optically-transparent substrate 1010, underlayers 1030A, 1030B, and 1030C must be made of a material with substantially the same index of refraction as that of optically-transparent substrate 1010. For example, if the material of the optically-transparent substrate 1010 is DUV grade silica, then underlayers 1030A, 1030B, and 1030C may be formed of $SiO_2$ which has substantially the same index of refraction.

To minimize dispersion at the zone joint between the zone lacking a thin-film stack filter, and the adjacent zone having thin-film stack filter 1020B deposited thereupon, the thicknesses of underlayers 1030A and 1030B are adjusted such that the traversed optical length across thin-film stack filter 1020B and underlayer 1030B, is equal to the traversed optical length across only underlayer 1030A of the adjacent zone. Alternatively, as explained before, the requirement for phase matching of emerging beams at the zone joint may be satisfied by making the thicknesses of underlayers 1030A and 1030B such that the traversed optical length of wavelength $\lambda_j$ incident at the zone joint, across thin-film stack filter 1020B and underlayer 1030B, differs from the traversed optical length across only underlayer 1030A of the adjacent zone, by an integer number of wavelengths $\lambda_j$. In similar vein, to minimize dispersion at the zone joint between thin-film stack filters 1020B and 1020C, the thicknesses of underlayers 1030B and 1030C are adjusted such that the traversed optical length across thin-film stack filter 1020C and underlayer 1030C, is equal to the traversed optical length across thin-film stack filter 1020B and underlayer 1030B, of the adjacent zone. Alternatively, the requirement for phase matching of emerging beams at the zone joint may be satisfied by making the thicknesses of underlayers 1030B and 1030C such that the traversed optical length of wavelength $\lambda_j$ incident at the zone joint, across thin-film stack filter 1020C and underlayer 1030C, differs from the traversed optical length across thin-film stack filter 1020B and underlayer 1030B, of the adjacent zone, by an integer number of wavelengths $\lambda_j$. In this fashion, the transmitted beam 1008 emerges from all OSF zones "in phase" across zone joints, and dispersion at the zone joints is minimized. In determining the thicknesses of underlayers 1030A, 1030B, and 1030C, the angle of incidence of incident beam 1005 needs to be taken into account, as it affects the traversed optical lengths.

The OSF zone with underlayer 1030A, which lacks a thin-film stack filter, has high light transmission, and can be used, for example, for the UV and DUV part of the spectrum, where transmission losses are high and signal levels low in typical optical metrology systems. The remaining zones can be used for near ultraviolet, visible (VIS) and near-infrared (NIR) parts of the spectrum, where transmission losses and signal levels present less of a concern.

Figure 11:
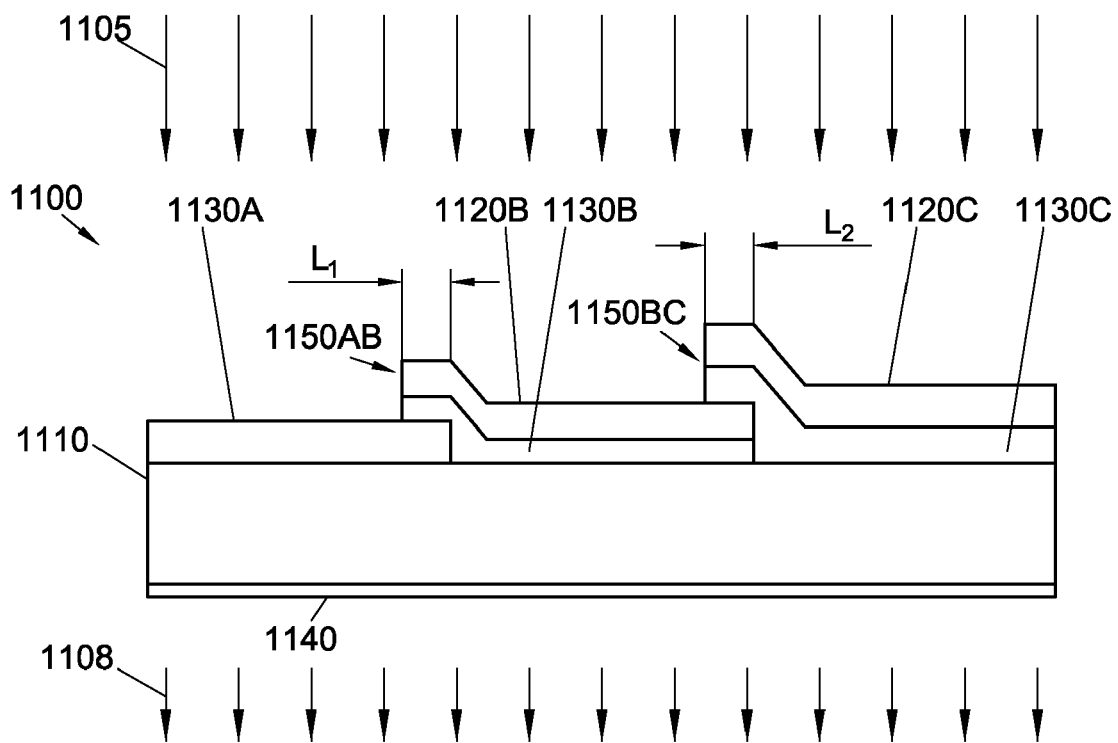
FIG. 11 is a schematic representation of a diffraction order sorting filter in accordance with another embodiment of the invention.

FIG. 11 shows an embodiment 1100 of, for example, order sorting filter (OSF) 570 of FIG. 5. OSF 1100 has three zones, of which the first one does not have a thin-film stack filter deposited thereupon. The passbands of the remaining two zones are determined by thin-film stack filters 1120B and 1120C respectively, all deposited on a common optically-transparent substrate 1110. The optically-transparent substrate 1110 can be made of DUV grade silica, to allow for high transmission in the UV and DUV parts of the spectrum, but other materials can also be used, such as various types of glass, quartz, calcium-fluoride, sapphire, etc. An antireflective coating 1140 may be applied to the side of optically-transparent substrate opposite the thin-film stack filters 1120B and 1120C, to minimize light reflections at the substrate-to-air interface. Thin-film stack filters 1120B and 1120C are made of multiple thin films, whose thicknesses and materials determine their passband.

Incident light beam 1105 is transmitted through thin-film stack filters 1120B and 1120C, the optically-transparent substrate 1110, and the optional antireflective coating 1140, to form the transmitted beam 1108. Incident beam 1105 and transmitted beam 1108 may propagate perpendicular to the surface of OSF 1100, as is shown in FIG. 11, or they may propagate at angles not normal with respect to the surface of OSF 1100, as the spectrometer design and mounting angles of the OSF may dictate. As mentioned before, in a prior art OSF, the optical length traversed by incident beam 1105 across the entire OSF 1100 will vary from one zone to another, causing dispersion at the zone joints and the emergence of transmitted beam 1108 that underwent different phase changes while traversing the two zones adjacent a zone joint. To correct this, underlayers 1130A, 1130B, and 1130C are deposited on optically-transparent substrate 1110 before the deposition of thin-film stack filters 1120B and 1120C respectively. To reduce internal reflections at the interface between the underlayers 1130A, 1130B, 1130C, and the optically-transparent substrate 1110, underlayers 1130A, 1130B, and 1130C must be made of a material with substantially the same index of refraction as that of optically-transparent substrate 1110. For example, if the material of the optically-transparent substrate 1110 is DUV grade silica, then underlayers 1130A, 1130B, and 1130C may be formed of $SiO_2$ which has substantially the same index of refraction.

To minimize dispersion at the zone joint between the zone lacking a thin-film stack filter, and the adjacent zone having thin-film stack filter 1120B deposited thereupon, the thicknesses of underlayers 1130A and 1130B are adjusted such that the traversed optical length across thin-film stack filter 1120B and underlayer 1130B, is equal to the traversed optical length across only underlayer 1130A of the adjacent zone. Alternatively, as explained before, the requirement for phase matching of emerging beams at the zone joint may be satisfied by making the thicknesses of underlayers 1130A and 1130B such that the traversed optical length of wavelength $\lambda_j$ incident at the zone joint, across thin-film stack filter 1120B and underlayer 1130B, differs from the traversed optical length across only underlayer 1130A of the adjacent zone, by an integer number of wavelengths $\lambda_j$. In similar vein, to minimize dispersion at the zone joint between thin-film stack filters 1120B and 1120C, the thicknesses of underlayers 1130B and 1130C are adjusted such that the traversed optical length across thin-film stack filter 1120C and underlayer 1130C, is equal to the traversed optical length across thin-film stack filter 1120B and underlayer 1130B, of the adjacent zone. Alternatively, the requirement for phase matching of emerging beams at the zone joint may be satisfied by making the thicknesses of underlayers 1130B and 1130C such that the traversed optical length of wavelength $\lambda_j$ incident at the zone joint, across thin-film stack filter 1120C and underlayer 1130C, differs from the traversed optical length across thin-film stack filter 1120B and underlayer 1130B, of the adjacent zone, by an integer number of wavelengths $\lambda_j$. In this fashion, the transmitted beam 1108 emerges from all OSF zones "in phase" across zone joints, and dispersion at the zone joints is minimized. In determining the thicknesses of underlayers 1130A, 1130B, and 1130C, the angle of incidence of incident beam 1105 needs to be taken into account, as it affects the traversed optical lengths.

Unlike OSF 1000 of FIG. 10, OSF 1100 of FIG. 11 is manufactured with somewhat relaxed manufacturing tolerances, which allow the formation of overlaps 1150AB and 1150BC, atop of the zone joints. In these overlaps, both an underlayer and a thin-film stack filter are allowed to overlap an adjacent zone in which the underlayer and/or thin-film stack filter have already been deposited. The widths of overlaps 1150AB and 1150BC, $L_1$ and $L_2$ respectively, can vary, for example, from 0 to 400 µm, or alternatively from 0 to 200 µm. Depending on the OSF manufacturing process, tolerances may also allow the formation of gaps between zones, instead of overlaps 1150AB and 1150BC. Also, the OSF zone with underlayer 1130A, which lacks a thin-film stack filter, has high light transmission, and can be used, for example, for the UV and DUV part of the spectrum, where transmission losses are high and signal levels low in typical optical metrology systems. The remaining zones can be used for near ultraviolet, visible (VIS) and near-infrared (NIR) parts of the spectrum, where transmission losses and signal levels present less of a concern.

Figure 12:
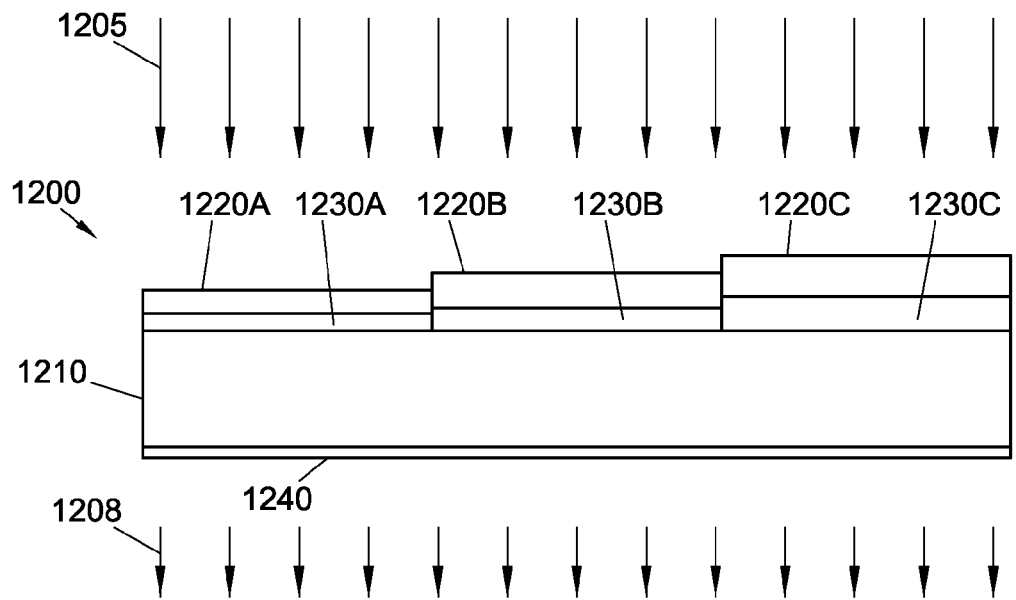
FIG. 12 is a schematic representation of a diffraction order sorting filter in accordance with yet another embodiment of the invention.

FIG. 12 shows an embodiment 1200 of, for example, order sorting filter (OSF) 570 of FIG. 5. OSF 1200 has three zones, the passbands of which are determined by thin-film stack filters 1220A, 1220B, and 1220C respectively, all deposited on a common optically-transparent substrate 1210. The optically-transparent substrate 1210 can be made of DUV grade silica, to allow for high transmission in the UV and DUV parts of the spectrum, but other materials can also be used, such as various types of glass, quartz, calcium-fluoride, sapphire, etc. An antireflective coating 1240 may be applied to the side of optically-transparent substrate opposite the thin-film stack filters 1220A, 1220B, and 1220C, to minimize light reflections at the substrate-to-air interface. Thin-film stack filters 1220A, 1220B, and 1220C are made of multiple thin films, whose thicknesses and materials determine their passband.

Incident light beam 1205 is transmitted through thin-film stack filters 1220A, 1220B, and 1220C, the optically-transparent substrate 1210, and the optional antireflective coating 1240, to form the transmitted beam 1208. Incident beam 1205 and transmitted beam 1208 may propagate perpendicular to the surface of OSF 1200, as is shown in FIG. 12, or they may propagate at angles not normal with respect to the surface of OSF 1200, as the spectrometer design and mounting angles of the OSF may dictate. As mentioned before, in a prior art OSF, the optical length traversed by incident beam 1205 across the entire OSF 1200 will vary from one zone to another, causing dispersion at the zone joints and the emergence of transmitted beam 1208 that underwent different phase changes while traversing the two zones adjacent a zone joint. To correct this, underlayers 1230A, 1230B, and 1230C are deposited on optically-transparent substrate 1210 before the deposition of thin-film stack filters 1220A, 1220B, and 1220C respectively. To reduce internal reflections at the interface between the underlayers 1230A, 1230B, and 1230C, and the optically-transparent substrate 1210, underlayers 1230A, 1230B, and 1230C must be made of a material with substantially the same index of refraction as that of optically-transparent substrate 1210. For example, if the material of the optically-transparent substrate 1210 is DUV grade silica, then underlayers 1230A, 1230B, and 1230C may be formed of $SiO_2$ which has substantially the same index of refraction.

To minimize dispersion at the zone joint between zones having thin-film stack filters 1220A and 1220B deposited thereupon, the thicknesses of underlayers 1230A and 1230B are adjusted such that the traversed optical length across thin-film stack filter 1220B and underlayer 1230B, is equal to the traversed optical length across thin-film stack filter 1220A and underlayer 1230A of the adjacent zone. Alternatively, as explained before, the requirement for phase matching of emerging beams at the zone joint may be satisfied by making the thicknesses of underlayers 1230A and 1230B such that the traversed optical length of wavelength $\lambda_j$ incident at the zone joint, across thin-film stack filter 1220B and underlayer 1230B, differs from the traversed optical length across thin-film stack filter 1120A and underlayer 1230A of the adjacent zone, by an integer number of wavelengths $\lambda_j$. In similar vein, to minimize dispersion at the zone joint between thin-film stack filters 1220B and 1220C, the thicknesses of underlayers 1230B and 1230C are adjusted such that the traversed optical length across thin-film stack filter 1220C and underlayer 1230C, is equal to the traversed optical length across thin-film stack filter 1220B and underlayer 1230B, of the adjacent zone. Alternatively, the requirement for phase matching of emerging beams at the zone joint may be satisfied by making the thicknesses of underlayers 1230B and 1230C such that the traversed optical length of wavelength $\lambda_j$ incident at the zone joint, across thin-film stack filter 1220C and underlayer 1230C, differs from the traversed optical length across thin-film stack filter 1220B and underlayer 1230B, of the adjacent zone, by an integer number of wavelengths $\lambda_j$. In this fashion, the transmitted beam 1208 emerges from all OSF zones "in phase" across zone joints, and dispersion at the zone joints is minimized. In determining the thicknesses of underlayers 1230A, 1230B, and 1230C, the angle of incidence of incident beam 1205 needs to be taken into account, as it affects the traversed optical lengths.

Unlike OSF 800 of FIG. 8 and OSF 1000 of FIG. 10, OSF 1200 of FIG. 12 has an underlayer 1030A deposited underneath thin-film stack filter 1020A. This configuration has the advantage of allowing greater optical design and manufacturing flexibility because thicknesses of both underlayers 1030A and 1030B may be adjusted to achieve a traversed optical length match, or an "in phase" condition.

Figure 13:
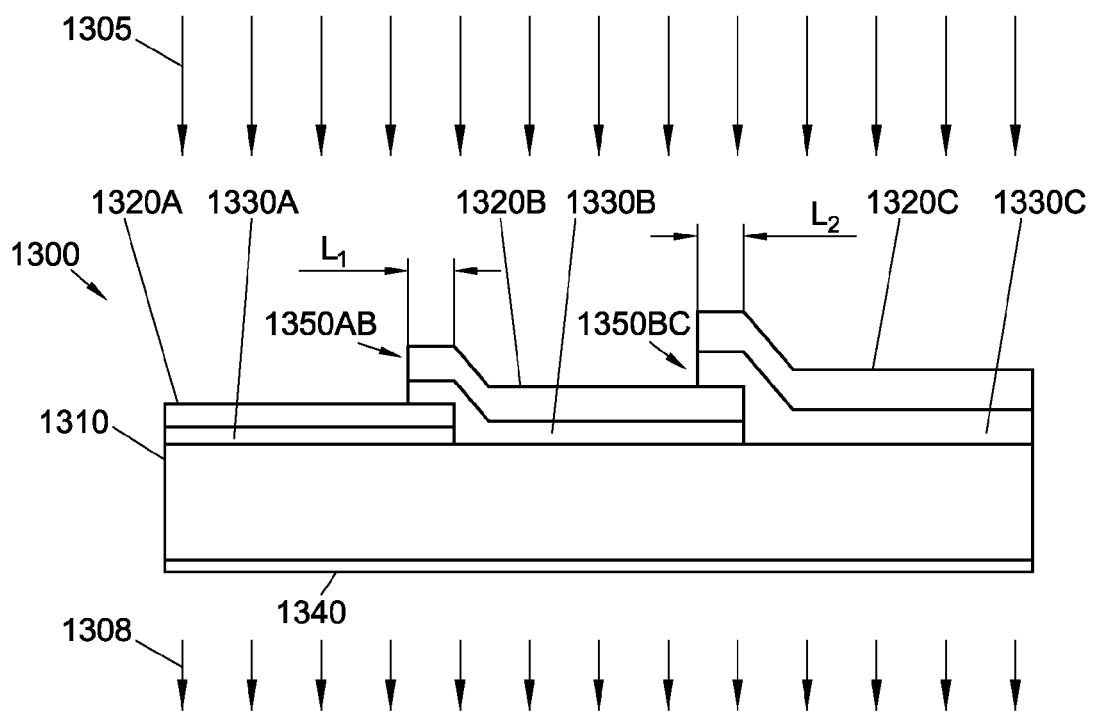
FIG. 13 is a schematic representation of a diffraction order sorting filter in accordance with yet another embodiment of the invention.

FIG. 13 shows an embodiment 1300 of, for example, order sorting filter (OSF) 570 of FIG. 5. OSF 1300 has three zones, the passbands of which are determined by thin-film stack filters 1320A, 1320B, and 1320C respectively, all deposited on a common optically-transparent substrate 1310. The optically-transparent substrate 1310 can be made of DUV grade silica, to allow for high transmission in the UV and DUV parts of the spectrum, but other materials can also be used, such as various types of glass, quartz, calcium-fluoride, sapphire, etc. An antireflective coating 1340 may be applied to the side of optically-transparent substrate opposite the thin-film stack filters 1320A, 1320B, and 1320C, to minimize light reflections at the substrate-to-air interface. Thin-film stack filters 1320A, 1320B, and 1320C are made of multiple thin films, whose thicknesses and materials determine their passband.

Incident light beam 1305 is transmitted through thin-film stack filters 1320A, 1320B, and 1320C, the optically-transparent substrate 1310, and the optional antireflective coating 1340, to form the transmitted beam 1308. Incident beam 1305 and transmitted beam 1308 may propagate perpendicular to the surface of OSF 1300, as is shown in FIG. 13, or they may propagate at angles not normal with respect to the surface of OSF 1300, as the spectrometer design and mounting angles of the OSF may dictate. As mentioned before, in a prior art OSF, the optical length traversed by incident beam 1305 across the entire OSF 1300 will vary from one zone to another, causing dispersion at the zone joints and the emergence of transmitted beam 1308 that underwent different phase changes while traversing the two zones adjacent a zone joint. To correct this, underlayers 1330A, 1330B, and 1330C are deposited on optically-transparent substrate 1310 before the deposition of thin-film stack filters 1320A, 1320B, and 1320C respectively. To reduce internal reflections at the interface between the underlayers 1330A, 1330B, 1330C, and the optically-transparent substrate 1310, underlayers 1330A, 1330B, and 1330C must be made of a material with substantially the same index of refraction as that of optically-transparent substrate 1310. For example, if the material of the optically-transparent substrate 1310 is DUV grade silica, then underlayers 1330A, 1330B, and 1330C may be formed of $SiO_2$ which has substantially the same index of refraction.

To minimize dispersion at the zone joint between zones having thin-film filter stacks 1320A and 1320B deposited thereupon, the thicknesses of underlayers 1330A and 1330B are adjusted such that the traversed optical length across thin-film stack filter 1320B and underlayer 1330B, is equal to the traversed optical length across thin-film stack filter 1320A and underlayer 1330A of the adjacent zone. Alternatively, as explained before, the requirement for phase matching of emerging beams at the zone joint may be satisfied by making the thicknesses of underlayers 1330A and 1330B such that the traversed optical length of wavelength $\lambda_j$ incident at the zone joint, across thin-film stack filter 1320B and underlayer 1330B, differs from the traversed optical length across thin-film stack filter 1320A and underlayer 1330A of the adjacent zone, by an integer number of wavelengths $\lambda_j$. In similar vein, to minimize dispersion at the zone joint between thin-film stack filters 1320B and 1320C, the thicknesses of underlayers 1330B and 1330C are adjusted such that the traversed optical length across thin-film stack filter 1320C and underlayer 1330C, is equal to the traversed optical length across thin-film stack filter 1320B and underlayer 1330B, of the adjacent zone. Alternatively, the requirement for phase matching of emerging beams at the zone joint may be satisfied by making the thicknesses of underlayers 1330B and 1330C such that the traversed optical length of wavelength $\lambda_j$ incident at the zone joint, across thin-film stack filter 1320C and underlayer 1330C, differs from the traversed optical length across thin-film stack filter 1320B and underlayer 1330B, of the adjacent zone, by an integer number of wavelengths $\lambda_j$. In this fashion, the transmitted beam 1308 emerges from all OSF zones "in phase" across zone joints, and dispersion at the zone joints is minimized. In determining the thicknesses of underlayers 1330A, 1330B, and 1330C, the angle of incidence of incident beam 1305 needs to be taken into account, as it affects the traversed optical lengths.

Unlike OSF 900 of FIG. 9 and OSF 1100 of FIG. 11, OSF 1300 of FIG. 13 has an underlayer 1330A deposited underneath thin-film stack filter 1320A. This configuration has the advantage of allowing greater optical design and manufacturing flexibility because thicknesses of both underlayers 1330A and 1330B may be adjusted to achieve a traversed optical length match, or an "in phase" condition.

Unlike OSF 1200 of FIG. 12, OSF 1300 of FIG. 13 is manufactured with somewhat relaxed manufacturing tolerances, which allow the formation of overlaps 1350AB and 1350BC, atop of the zone joints. In these overlaps, both an underlayer and a thin-film stack filter are allowed to overlap an adjacent zone in which the underlayer and/or thin-film stack filter have already been deposited. The widths of overlaps 1350AB and 1350BC, $L_1$ and $L_2$ respectively, can vary, for example, from 0 to 400 µm, or alternatively from 0 to 200 µm. Depending on the OSF manufacturing process, tolerances may also allow the formation of gaps between zones, instead of overlaps 1350AB and 1350BC.

Figure 14:
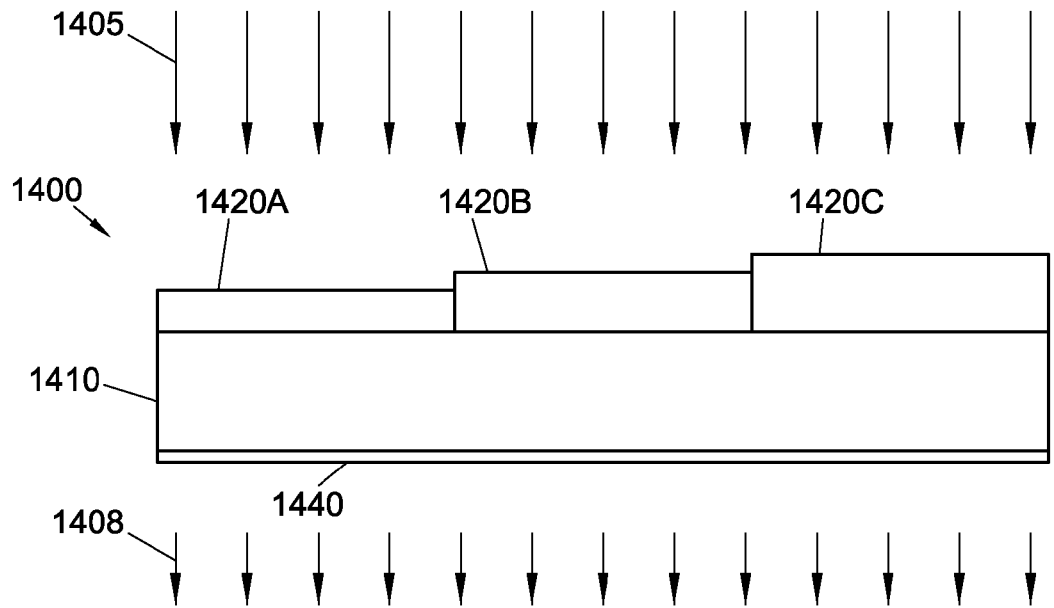
FIG. 14 is a schematic representation of a diffraction order sorting filter in accordance with yet a further embodiment of the invention.

FIG. 14 shows an embodiment 1400 of, for example, order sorting filter (OSF) 570 of FIG. 5. OSF 1400 has three zones, whose passbands are determined by thin-film stack filters 1420A, 1420B, and 1420C respectively, all deposited on a common optically-transparent substrate 1410. The optically-transparent substrate 1410 can be made of DUV grade silica, to allow for high transmission in the UV and DUV parts of the spectrum, but other materials can also be used, such as various types of glass, quartz, calcium-fluoride, sapphire, etc. An antireflective coating 1440 may be applied to the side of optically-transparent substrate opposite the thin-film stack filters 1420A, 1420B, and 1420C, to minimize light reflections at the substrate-to-air interface. Thin-film stack filters 1420A, 1420B, and 1420C are made of multiple thin films, whose thicknesses and materials determine their passband.

Incident light beam 1405 is transmitted through thin-film stack filters 1420A, 1420B, 1420C, the optically-transparent substrate 1410, and the optional antireflective coating 1440, to form the emerging transmitted beam 1408. Incident beam 1405 and transmitted beam 1408 may propagate perpendicular to the surface of OSF 1400, as is shown in FIG. 14, or they may propagate at angles not normal with respect to the surface of OSF 1400, as the spectrometer design and mounting angles of the OSF may dictate. As mentioned before, in a prior art OSF, the optical length traversed by incident beam 1405 across the entire OSF 1400 will vary from one zone to another, causing dispersion at the zone joints and the emergence of transmitted beam 1408 that underwent different phase changes while traversing the different OSF zones. To correct this, in addition to being designed to have a desired passband, thin-film stack filters 1420A, 1420B, and 1420C are designed such that the traversed optical lengths across them satisfy conditions to minimize dispersion at zone joints. The process of designing thin-film stack filters given a set of known passband requirements and additional constraints, such as specifying the traversed optical length across the filter, in addition to the passband, is well known in the optical arts, and will not be further discussed herein.

To minimize dispersion at the zone joint between thin-film stack filters 1420A and 1420B, thin-film stack filters 1420A and 1420B are designed to have the same optical thickness. Alternatively, as explained before, the requirement for phase matching of emerging beams at the zone joint may be satisfied by designing thin-film stack filters 1420A and 1420B such that the traversed optical length of wavelength $\lambda_j$ incident at the zone joint, across thin-film stack filters 1420B, differs from the traversed optical length across thin-film stack filter 1420A, of the adjacent zone, by an integer number of wavelengths $\lambda_j$. In similar vein, to minimize dispersion at the zone joint between thin-film stack filters 1420B and 1420C, thin-film stack filters 1420B and 1420C are designed to have the same optical thickness. Alternatively, as explained before, the requirement for phase matching of emerging beams at the zone joint may be satisfied by designing thin-film stack filters 1420B and 1420C such that the traversed optical length of wavelength $\lambda_j$ incident at the zone joint, across thin-film stack filter 1420C, differs from the traversed optical length across thin-film stack filter 1420B, of the adjacent zone, by an integer number of wavelengths $\lambda_j$. In this fashion, the transmitted beam 1408 emerges from all OSF zones "in phase", and dispersion at the zone joints is minimized. In designing the thin-film stack filters 1420A, 1420B, and 1420C, to satisfy the requirements for minimizing dispersion at a zone joint, the angle of incidence of incident beam 1405 needs to be taken into account, as it affects the traversed optical lengths.

Unlike OSF 800 of FIG. 8, OSF 1000 of FIG. 10, and OSF 1200 of FIG. 12, OSF 1400 of FIG. 14 does not utilize any underlayers next to the optically-transparent substrate to achieve a match of traversed optical lengths, or a "phase match". This simplifies the OSF manufacturing process by removing, in this example, two or three underlayer deposition steps, at the expense of somewhat increased complexity of the optical design of the thin-film stack filters themselves.

Figure 15:
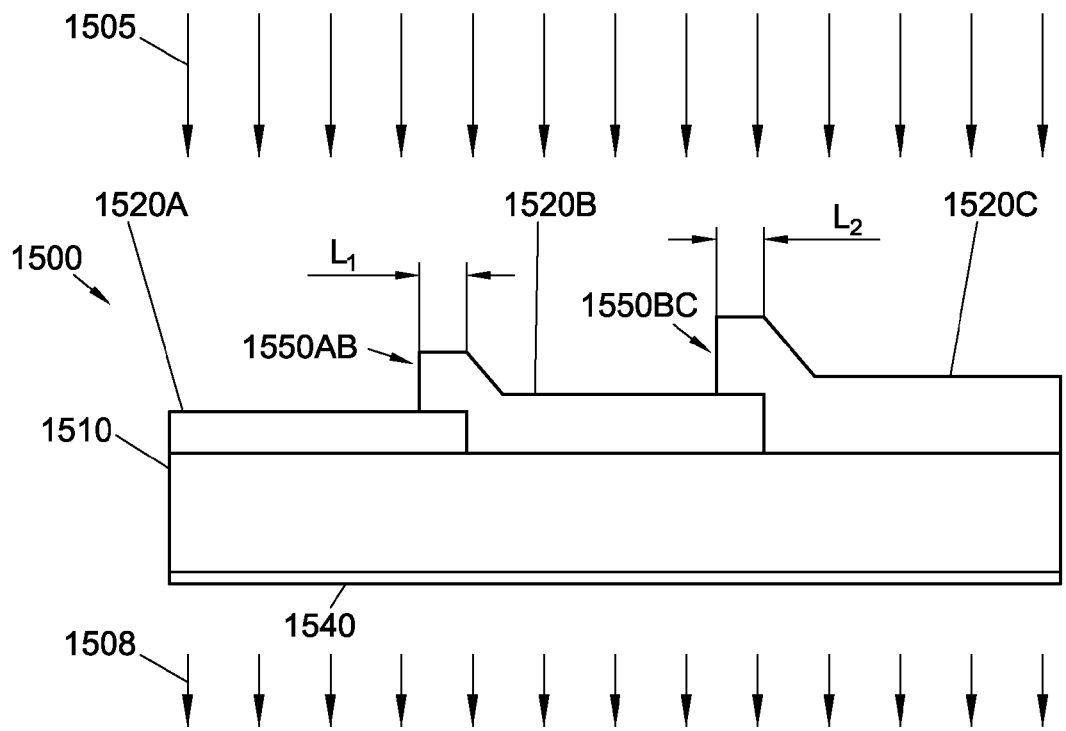
FIG. 15 is a schematic representation of a diffraction order sorting filter in accordance with yet a further embodiment of the invention.

FIG. 15 shows an embodiment 1500 of, for example, order sorting filter (OSF) 570 of FIG. 5. OSF 1500 has three zones, whose passbands are determined by thin-film stack filters 1520A, 1520B, and 1520C respectively, all deposited on a common optically-transparent substrate 1510. The optically-transparent substrate 1510 can be made of DUV grade silica, to allow for high transmission in the UV and DUV parts of the spectrum, but other materials can also be used, such as various types of glass, quartz, calcium-fluoride, sapphire, etc. An antireflective coating 1540 may be applied to the side of optically-transparent substrate opposite the thin-film stack filters 1520A, 1520B, and 1520C, to minimize light reflections at the substrate-to-air interface. Thin-film stack filters 1520A, 1520B, and 1520C are made of multiple thin films, whose thicknesses and materials determine their passband.

Incident light beam 1505 is transmitted through thin-film stack filters 1520A, 1520B, 1520C, the optically-transparent substrate 1510, and the optional antireflective coating 1540, to form the emerging transmitted beam 1508. Incident beam 1505 and transmitted beam 1508 may propagate perpendicular to the surface of OSF 1500, as is shown in FIG. 15, or they may propagate at angles not normal with respect to the surface of OSF 1500, as the spectrometer design and mounting angles of the OSF may dictate. As mentioned before, in a prior art OSF, the optical length traversed by incident beam 1505 across the entire OSF 1500 will vary from one zone to another, causing dispersion at the zone joints and the emergence of transmitted beam 1508 that underwent different phase changes while traversing the different OSF zones. To correct this, in addition to being designed to have a desired passband, thin-film stack filters 1520A, 1520B, and 1520C are designed such that the traversed optical lengths across them satisfy conditions to minimize dispersion at zone joints.

To minimize dispersion at the zone joint between thin-film stack filters 1520A and 1520B, thin-film stack filter 1520B is designed to have the same optical thickness as thin-film stack filter 1520A of the adjacent zone. Alternatively, as explained before, the requirement for phase matching of emerging beams at the zone joint may be satisfied by designing thin-film stack filter 1520B such that the traversed optical length of wavelength $\lambda_j$ incident at the zone joint, across thin-film stack filter 1520B, differs from the traversed optical length across thin-film stack filter 1520A, of the adjacent zone, by an integer number of wavelengths $\lambda_j$. In similar vein, to minimize dispersion at the zone joint between thin-film stack filters 1520B and 1520C, thin-film stack filter 1520C is designed to have the same optical thickness as thin-film stack filter 1520B of the adjacent zone. Alternatively, as explained before, the requirement for phase matching of emerging beams at the zone joint may be satisfied by designing thin-film stack filters 1520B and 1520C such that the traversed optical length of wavelength $\lambda_j$ incident at the zone joint, across thin-film stack filter 1520C, differs from the traversed optical length across thin-film stack filter 1520B, of the adjacent zone, by an integer number of wavelengths $\lambda_j$. In this fashion, the transmitted beam 1508 emerges from all OSF zones "in phase", and dispersion at the zone joints is minimized. In designing the thin-film stack filters 1520A, 1520B, and 1520C, to satisfy the requirements for minimizing dispersion at a zone joint, the angle of incidence of incident beam 1505 needs to be taken into account, as it affects the traversed optical lengths.

Unlike OSF 1400 of FIG. 14, OSF 1500 of FIG. 15 is manufactured with somewhat relaxed manufacturing tolerances, which allow the formation of overlaps 1550AB and 1550BC, atop of the zone joints. In these overlaps, a thin-film stack filter is allowed to overlap an adjacent zone in which a thin-film stack filter has already been deposited. The widths of overlaps 1350AB and 1350BC, $L_1$ and $L_2$ respectively, can vary, for example, from 0 to 400 μm, or alternatively from 0 to 200 μm. Depending on the OSF manufacturing process, tolerances may also allow the formation of gaps between zones, instead of overlaps 1550AB and 1550BC. Also, unlike OSF 900 of FIG. 9, OSF 1100 of FIG. 11, and OSF 1300 of FIG. 13, OSF 1500 of FIG. 15 does not utilize any underlayers next to the optically-transparent substrate to achieve a match of traversed optical lengths, or a "phase match". This simplifies the OSF manufacturing process by removing, in this example, two or three underlayer deposition steps, at the expense of somewhat increased complexity of the optical design of the thin-film stack filters themselves.

Those skilled in the optical arts will immediately recognize that an optical design may be created which combines features of the eight OSF embodiments of FIGS. 8-15. For example, one can design and use an OSF which will have no thin-film filter stack and only an underlayer in the first zone, to be used to transmit VUV and UV light; have an underlayer underneath a thin-film filter stack in the second zone; and have a third zone thin-film stack filter designed to satisfy the "in phase" condition at the zone joint between the second and third zones, without requiring an underlayer. It is immediately apparent that many such possible design combinations can be made, all of which are considered within the scope of the present invention.

Disclosed embodiments of order sorting filter (OSF) 800, 900, 1000, 1100, 1200, 1300, 1400, and 1500, of FIGS. 8-15 respectively, all minimize dispersion at zone joints to varying degrees, but may not entirely eliminate it. In particular, OSF embodiments 900, 1100, 1300, and 1500, of FIGS. 9, 11, and 13, which allow overlaps or gaps to be formed at zone joints, may have sufficient residual dispersion to warrant additional measures to improve the accuracy of measured diffraction signals. Residual dispersion may manifest itself by the formation of, for example, peak 700 in the graph of reflectance residual $R(\lambda)$, as previously explained and shown in FIG. 7. This highly-localized nonlinearity caused by dispersion at the zone joint, as mentioned before, cannot be captured and represented accurately using a $3^{rd}$ or $4^{th}$ order calibration polynomial that applies to all pixel locations of the array detector, and across all zones and zone joints of the OSF. To be able to eliminate peak 700, one has to be able to accurately represent the highly nonlinear and fast varying form of the wavelength to pixel location calibration curve, in the vicinity of zone joints.

Figure 17:
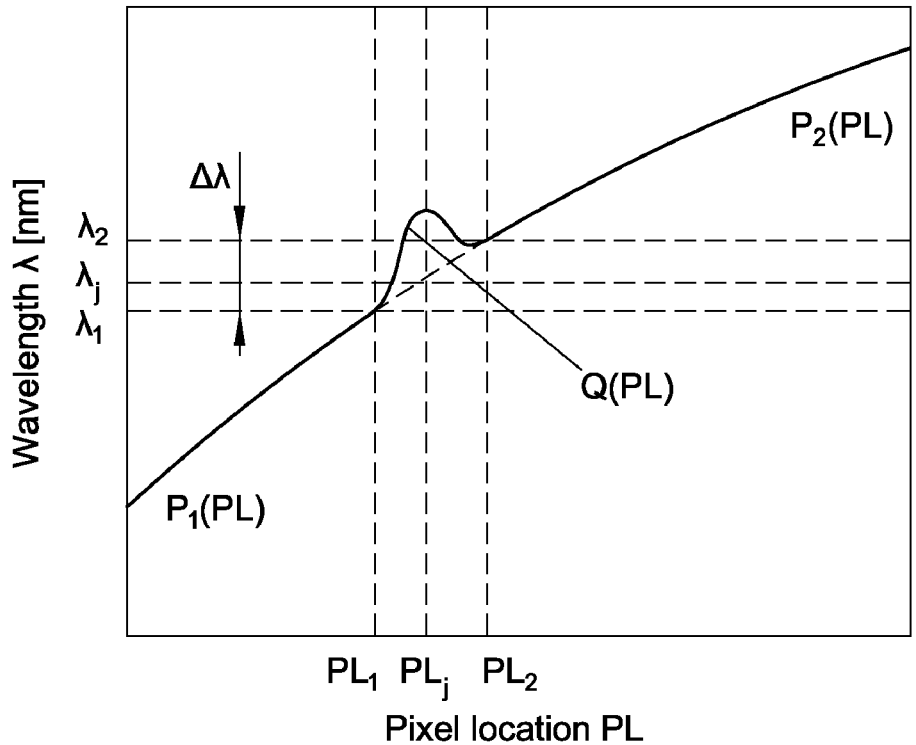
FIG. 17 is a graph of an exemplary wavelength to pixel location calibration curve fit wherein a separate calibration is used in the vicinity of an OSF zone joint to accommodate for dispersion caused by the OSF zone joint.

FIG. 17 presents a solution of this problem that the inventors have discovered. In the graph in FIG. 17, the $3^{rd}$ or $4^{th}$ order polynomial wavelength to pixel location calibration curve $P(PL)$, where PL denotes a pixel location, remains valid over all wavelengths $\lambda$ seen by the array detector, except over wavelength range $\Delta\lambda=\lambda_2-\lambda_1$, corresponding to pixel location range $PL_1$ to $PL_2$, inside which the calibration curve is affected by dispersion at the zone joint whose location corresponds to incident wavelength $\lambda_j$ on the array detector, or pixel location $PL_j$. Depending on the nature of dispersion at the zone joint, incident wavelength at the zone joint $\lambda_j$ may be located at the center of wavelength range $\Delta\lambda=\lambda_2-\lambda_1$, such as when there is no appreciable shift of the centroid of the image projected upon the array detector, at the zone joint. However, if the centroid of the image projected upon the array detector, at the zone joint, is shifted sideways, as explained before, then wavelength at the zone joint $\lambda_j$ will, in general, not be centered within wavelength range $\Delta\lambda=\lambda_2-\lambda_1$.

To maintain an accurate representation of the actual wavelength to pixel location calibration curve, including the effects of dispersion, the calibration curve is split into three parts at each zone joint: polynomial $P_1(PL)$ of pixel location PL, valid for wavelengths $\lambda$ lower than $\lambda_1$ (i.e. for pixel locations lower than $PL_1$), polynomial $P_2(PL)$ of pixel location PL, valid for wavelengths $\lambda$ higher than $\lambda_2$ (i.e. for pixel locations higher than $PL_2$), and function $Q(PL)$ of pixel location PL, used to represent the calibration curve portion affected by dispersion within the wavelength range $\Delta\lambda=\lambda_2-\lambda_1$ (i.e. over pixel location range $PL_1$ through $PL_2$). In this calibration method, fit coefficients of polynomials $P_1(PL)$ and $P_2(PL)$ can be made equal, i.e. $P_1(PL)=P_2(PL)=P(PL)$, or alternatively, polynomials $P_1(PL)$ and $P_2(PL)$ may be allowed to have different sets of fit coefficients. Function $Q(PL)$ may be represented in the form of a polynomial, for example, of order 2 through 10, or alternatively order 2 through 6, or alternatively yet order 2 through 4, the relatively high order of the polynomial is to allow the capture of the highly nonlinear nature of the calibration curve within wavelength range $\Delta\lambda=\lambda_2-\lambda_1$ (i.e. over pixel location range $PL_1$ through $PL_2$).

Alternatively, function $Q(PL)$ may be represented as a non-polynomial mathematical function of pixel location PL, or a series of mathematical functions of pixel location PL, all of which should have defined constants which can be used in lieu of fit coefficients of the polynomial form of $Q(PL)$, to allow adjustment of the calibration curve fit. For example, the function $Q(PL)$, or a member of the series $Q(PL)$, can be in the form of a Gaussian, or a generalized exponential function defined by $$\lambda=Q(PL)=(A\cdot PL+B)e^{-(C\cdot PL+D)^2}+E,$$

where A, B, C, D, and E, are fit constants. Alternatively yet, instead of as a polynomial or some other non-polynomial mathematical function, or series of functions, function $Q(PL)$ may be represented as a lookup table of discrete data points, each consisted of a pixel location-wavelength data pair, wherein each data pair can be adjusted to create the best fit calibration. During calculations, interpolation may be used to estimate values between the discrete data points of the lookup table.

During the previously described iterative calibration process, the fit coefficients of polynomials $P_1(PL)$ and $P_2(PL)$, and the polynomial or non-polynomial function, or series of functions $Q(PL)$, or alternatively lookup table data values for $Q(PL)$, are all adjusted together in an iterative fitting process so as to minimize the RMS reflectance residual calculated over the full range of wavelengths detected by the array detector. With the nonlinearity of the calibration curve at the zone joint well represented by function $Q(PL)$, the peak 700 of reflectance residual $R(\lambda)$, of FIG. 7, can be significantly reduced, or altogether eliminated. During the fitting process, additional constraints may be imposed on the fit coefficients, such as the requirement that the values of polynomial $P_1(PL)$ and function $Q(PL)$ match at wavelength $\lambda_1$ (i.e. pixel location $PL_1$), and similarly that the values of polynomial $P_2(PL)$ and function $Q(PL)$ match at wavelength $\lambda_2$ (i.e. pixel location $PL_2$). In addition to matching values, conditions may further be imposed to match the first and/or second derivatives of the calibration curve at wavelengths $\lambda_1$ and $\lambda_2$ (i.e. at pixel locations $PL_1$ and $PL_2$) in order to produce a smooth calibration curve, etc.

FIG. 17 described the method of splitting and fitting the calibration curve at a single zone joint. For a multi-zone OSF, multiple functions $Q_i(PL)$ are required to characterize the calibration curve at each zone joint i, and also multiple polynomials $P_k(PL)$ are required to describe the k=i+1 wavelength ranges not affected by dispersion at zone joints. For example, for an OSF with three zones and two zone joints, i=2, and k=3. Fit coefficients of all polynomials and functions need to be adjusted simultaneously during the iterative calibration process, along with performing the intensity calibration, to produce a good calibration curve that will allow subsequent accurate measurement of diffraction signals.

While polynomials are typically used to represent the calibration curves $P_1(PL)$ and $P_2(PL)$, in some cases it may be advantageous to replace polynomials $P_1(PL)$ and $P_2(PL)$ with non-polynomial functions of variable PL, or series of functions of variable PL, such as Gaussians, generalized exponential functions, or lookup tables, similar to the previously-described approaches taken with the function $Q(PL)$ in the vicinity of a zone joint. Generally, since the wavelength to pixel location calibration curve $P(PL)$ is smoother between zone joints than in the vicinity of zone joints, the fitting functions used for $P_1(PL)$ and $P_2(PL)$ will be smoother than $Q(PL)$. In all other respects the piecewise-defined calibration curve fitting process is the same as discussed previously using polynomial forms of $P_1(PL)$ and $P_2(PL)$ as examples.

Reference throughout this specification to "one embodiment" or "an embodiment" means that a particular feature, structure, material, or characteristic described in connection with the embodiment is included in at least one embodiment of the invention, but do not denote that they are present in every embodiment. Thus, the appearances of the phrases "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Various operations will be described as multiple discrete operations in turn, in a manner that is most helpful in understanding the invention. However, the order of description should not be construed as to imply that these operations are necessarily order dependent. In particular, these operations need not be performed in the order of presentation. Operations described may be performed in a different order than the described embodiment. Various additional operations may be performed and/or described operations may be omitted in additional embodiments.

Persons skilled in the relevant art can appreciate that many modifications and variations are possible in light of the above teaching. Persons skilled in the art will recognize various equivalent combinations and substitutions for various components shown in the figures. It is therefore intended that the scope of the invention be limited not by this detailed description, but rather by the claims appended hereto.

What is claimed is:

1. A method for wavelength to pixel location calibration of a spectrometer of an optical metrology system, comprising:
    providing an optical metrology system, comprising:
        a spectrometer having an array detector with pixel locations defined thereupon, for measuring diffraction spectra;
        an order sorting filter with at least two zones created thereon, each pair of adjacent zones of the order sorting filter defining zone joints therebetween,
    providing at least one metrology sample with known reflectance versus wavelength data,
    measuring the reflectance of the at least one metrology sample using the optical metrology system,
    defining a wavelength to pixel location calibration curve as a set of curves comprising:
        at least one first function of array detector pixel location that defines a portion of the wavelength to pixel location calibration curve affected by dispersion at an order sorting filter zone joint, the at least one first function containing adjustable fit coefficients; and
        at least two second functions of array detector pixel location that define portions of the wavelength to pixel location calibration curve not affected by dispersion at an order sorting filter zone joint, the at least two second functions containing adjustable fit coefficients,
    iteratively fitting adjustable fit coefficients of the at least one first function and the at least two second functions defining the wavelength to pixel location calibration curve to the measured reflectance data of the at least one metrology sample, and
    utilizing the fitted wavelength to pixel location calibration curve in subsequent measurement of diffraction spectra.

2. The method of claim 1, wherein a pixel intensity calibration is performed concurrently during the step of iteratively fitting adjustable fit coefficients.

3. The method of claim 1, wherein the at least two second functions are polynomials of array detector pixel location of order in the range of 3 to 4.

4. The method of claim 1, wherein the at least two second functions are non-polynomial mathematical functions.

5. The method of claim 1, wherein the at least two second functions are series of non-polynomial mathematical functions.

6. The method of claim 1, wherein the at least two second functions are represented by lookup tables containing pixel location-wavelength data pairs.

7. The method of claim 1, wherein the at least one first function of array detector pixel location is a polynomial of order in the range of 2 to 10.

8. The method of claim 1, wherein the at least one first function of array detector pixel location is a polynomial of order in the range of 2 to 6.

9. The method of claim 1, wherein the at least one first function of array detector pixel location is a polynomial of order in the range of 2 to 4.

10. The method of claim 1, wherein the at least one first function of array detector pixel location is a non-polynomial mathematical function.

11. The method of claim 10, wherein the at least one first function of array detector pixel location is a Gaussian.

12. The method of claim 10, wherein the at least one first function of array detector pixel location is a generalized exponential function.

13. The method of claim 1, wherein the at least one first function of array detector pixel location is a series of non-polynomial mathematical functions.

14. The method of claim 13, wherein the at least one first function of array detector pixel location is a series of Gaussians.

15. The method of claim 13, wherein the at least one first function of array detector pixel location is a series of generalized exponential functions.

16. The method of claim 1, wherein the at least one first function of array detector pixel location is represented by a lookup table containing pixel location-wavelength data pairs.

* * * * *